(12) United States Patent
Velin et al.

(10) Patent No.: US 9,078,914 B2
(45) Date of Patent: *Jul. 14, 2015

(54) METHOD FOR THE PREPARATION OF MICRO-RNA AND ITS THERAPEUTIC APPLICATION

(75) Inventors: Flemming Velin, Fredensborg (DK); Svend Lindenberg, Skodsborg (DK)

(73) Assignee: Velin-Pharma A/S, Fredensborg (DK)

( * ) Notice: Subject to any disclaimer, the term of this patent is extended or adjusted under 35 U.S.C. 154(b) by 21 days.

This patent is subject to a terminal disclaimer.

(21) Appl. No.: 13/394,649

(22) PCT Filed: Sep. 10, 2010

(86) PCT No.: PCT/EP2010/063313
§ 371 (c)(1),
(2), (4) Date: Mar. 7, 2012

(87) PCT Pub. No.: WO2011/029903
PCT Pub. Date: Mar. 17, 2011

(65) Prior Publication Data
US 2012/0172416 A1    Jul. 5, 2012

(30) Foreign Application Priority Data
Sep. 10, 2009 (EP) .................... 09169937

(51) Int. Cl.
| | |
|---|---|
| C07H 21/02 | (2006.01) |
| C07H 21/04 | (2006.01) |
| A61K 31/713 | (2006.01) |
| A61K 9/00 | (2006.01) |
| A61K 9/50 | (2006.01) |
| C12N 15/113 | (2010.01) |

(52) U.S. Cl.
CPC ............ *A61K 31/713* (2013.01); *A61K 9/0019* (2013.01); *A61K 9/5094* (2013.01); *C12N 15/113* (2013.01); *C12N 2310/141* (2013.01); *C12N 2330/10* (2013.01)

(58) Field of Classification Search
CPC .................................................. C12N 15/113
See application file for complete search history.

(56) References Cited

U.S. PATENT DOCUMENTS

| | | | |
|---|---|---|---|
| 2009/0124566 A1 | 5/2009 | Chi et al. | |
| 2011/0160290 A1* | 6/2011 | Tewari | ........................ 514/44 R |

FOREIGN PATENT DOCUMENTS

| | | |
|---|---|---|
| EP | 0740964 A1 | 11/1996 |
| JP | 2008-182921 A | 8/2008 |
| WO | WO 99/09051 A1 | 2/1999 |
| WO | WO 00/46249 A1 | 8/2000 |
| WO | WO 00/61256 A1 | 10/2000 |
| WO | WO 03/080122 A1 | 10/2003 |
| WO | WO 2004/026709 A1 | 4/2004 |
| WO | WO 2004/104553 A2 | 12/2004 |
| WO | WO 2006/007529 A2 | 1/2006 |
| WO | WO 2006/028967 A2 | 3/2006 |
| WO | WO 2007/090569 A1 | 8/2007 |
| WO | WO 2008/088858 A2 | 7/2008 |
| WO | WO 2008/095096 A2 | 8/2008 |
| WO | WO 2008/097230 A1 | 8/2008 |
| WO | WO 2008/116267 A1 | 10/2008 |
| WO | WO 2009/021325 A1 | 2/2009 |
| WO | WO 2009/033140 A1 | 3/2009 |
| WO | WO 2009/070653 A1 | 6/2009 |
| WO | WO 2009/104051 A3 | 8/2009 |
| WO | WO 2009/105044 A1 | 8/2009 |
| WO | WO 2010/118979 A1 | 10/2010 |

OTHER PUBLICATIONS

Koh, W., et al., Analysis of deep sequencing microRNA expression profile from human embryonic stem cells derived mesenchymal stem cells reveals possible role of let-7 microRNA family in downstream targeting of Hepatic Nuclear Factor 4 Alpha, BMC Genomics, Feb. 1, 2010, S6-1, xp002584983, Biomed Central, London, Great Britain.

Williams, A., et al., MicroRNA Expression Profiling in Mild Asthmatic Human Airways and Effect of Corticosteroid Therapy, PLOS One, Jun. 1, 2009, p. e5889 xp00914137, vol. 4(6), Public Library of Science, San Francisco, CA.

* cited by examiner

*Primary Examiner* — Amy Bowman
(74) *Attorney, Agent, or Firm* — Alston & Bird LLP

(57) ABSTRACT

The present invention relates to compositions comprising a therapeutically effective amount of miRNAs, their use for the treatment of medical conditions benefiting from being treated with these compositions, as well as methods for the preparation of compositions comprising miRNAs.

11 Claims, No Drawings

METHOD FOR THE PREPARATION OF MICRO-RNA AND ITS THERAPEUTIC APPLICATION

CROSS-REFERENCE TO RELATED APPLICATIONS

This application is the U.S. National Stage of International Application PCT/EP2010/063313 filed Sep. 10, 2010, which designates the U.S. and was published by the International Bureau in English on Mar. 17, 2011, and which claims the benefit of European Patent Application No. 09169937.1, filed Sep. 1, 2009, both of which are hereby incorporated by reference in their entirety.

FIELD OF THE INVENTION

The present invention relates to compositions comprising a therapeutically effective amount of miRNAs, their use for the treatment of medical conditions benefiting from being treated with these compositions. Also encompassed by the present invention are methods for the preparation of a composition comprising miRNAs.

BACKGROUND OF THE INVENTION

MicroRNAs (miRNAs) are short (about 21-24-nucleotides) noncoding RNAs that are thought to regulate gene expression through sequence-specific base pairing with target mRNAs. The underlying mechanism is still poorly understood, but it appears to involve the inhibition of translational initiation.

Many of the functional roles of microRNAs hint at the potential involvement of microRNAs in human disease, and as major regulators of growth and proliferation. As many microRNAs are de-regulated in primary human tumours, a role of microRNAs in human cancers has been suggested. Accordingly miRNA deficiencies or excesses have been correlated with a number of clinically important diseases ranging from myocardial infarction to cancers.

Potential roles of microRNAs in the development as well as the regulation of the immune system have also been suggested.

Inflammation, a key component of the immune system, functions in both defense (physiological) and in pathophysiological events to maintain the homeostasis of tissues, organs and individual cells. Acute inflammation is a short-term process characterized by the classic signs of inflammation, i.e. swelling, redness, pain, heat, and loss of function, due to infiltration of tissues by plasma of several activated components such as interleukins, antibodies, hormones etc. and leukocytes. It occurs as long as the injurious stimulus is present and ceases once the stimulus has been removed. Chronic inflammation is a pathological condition characterized by concurrent active inflammation, tissue destruction, and attempts at repair. Chronically inflamed tissue is characterized by the infiltration of mononuclear immune cells (monocytes, macrophages, lymphocytes, dendritic cells and other plasma cells), tissue destruction, and attempts at healing, which include angiogenesis and fibrosis.

Without inflammation, wounds and infections would not be able to heal and progressive destruction of the tissue would threaten the survival of the organism. Inappropriate inflammation, on the other hand, can lead to various diseases, including but not limited to indications such as hay fever, atherosclerosis, neurodegenerative diseases such as Alzheimer's, cancer and rheumatoid arthritis. For these reasons, inflammation is tightly regulated by the body.

Mononuclear immune cells are under infectious conditions attracted to the site of infection in an attempt to eliminate the foreign pathogen through phagocytosis. Leukocytes and dendritic cells are here activated by the pathogens to synthesize and release proinflammatory cytokines such as IL-1α, IL-1β, IL-3, IL-5, IL-6, IL-8, TNF-α(tumor necrosis factor-α), GM-CSF (granulocyte-macrophage colony-stimulating factor), NF-κB (nuclear factor kappa-light-chain-enhancer of activated B cells), and MCP-I (monocyte chemotactic protein-1). These released cytokines then further attract more immune cells to the infected site, amplifying the response of the immune system to defend the host against the foreign pathogen.

Dendritic cells are derived from hemopoietic bone marrow progenitor cells. These progenitor cells initially transform into immature dendritic cells. These cells are characterized by high endocytic activity and low T-cell activation potential. Immature dendritic cells constantly sample the surrounding environment for foreign pathogens. This is done through pattern recognition receptors such as the toll-like receptors (TLRs), which recognize specific chemical signatures found on subsets of pathogens. Once they have come into contact with a presentable antigen, they become activated into mature dendritic cells and begin to migrate to the lymph node. Immature dendritic cells phagocytize pathogens and degrade their proteins into small pieces and upon maturation present those fragments at their cell surface using MHC molecules. Simultaneously, they upregulate cell-surface receptors that act as co-receptors in T-cell activation. Once in the lymph nodes they act as antigen-presenting cells, in activating helper T-cells and killer T-cells as well as B-cells by presenting them with antigens derived from the pathogen, together with non-antigen specific co-stimulatory signals.

The biological role and in vivo functions of most mammalian miRNAs are still poorly understood and the underlying mechanisms of why and how miRNAs become deregulated are largely unknown.

Glucocorticoids (also referred to as "corticosteroids" or "steroidal drugs") as well as Nonsteroidal Antiinflammatory Drugs (NSAIDs) represent today one of the most effective clinical treatment for a range of inflammatory conditions, including acute inflammation. However, these drugs can have side effects that may threaten the overall health of the patient.

There remains a need to develop a safe, effective method of treating autoimmune diseases, inflammatory disorders, and cancers or other indications associated with abnormal cell growth or cell division. The present invention provides compositions and methods for treating such diseases and disorders.

OBJECT OF THE INVENTION

It is an object of embodiments of the invention to provide compositions suitable for the treatment of autoimmune diseases, inflammatory disorders, and cancers or other indications associated with abnormal cell growth or cell division, including but not limited to infertility, decreased sperm production, abortus habitualis and colitis.

SUMMARY OF THE INVENTION

It has been found by the present inventors that specific miRNA are upregulated in body fluids or element thereof upon activation or stimulation of cells or cell components in this body fluid or its elements and that compositions comprising miRNAs may be used for the treatment or for alleviating the symptoms of a disease, disorder or dysfunctions in the body, such as conditions associated with inflammation, a disease of the immune system, such as undesirable activation of the immune system and/or cancer or other indications associated with abnormal cell growth or cell division.

In a first aspect the present invention relates to a composition comprising a therapeutically effective amount of one or more miRNA molecule or functional variant thereof, said miRNA being upregulated in a body fluid or element thereof upon activation of said body fluid or element thereof; for the preparation of a medicament.

In a second aspect the present invention relates to a composition comprising a therapeutically effective amount of one or more miRNA molecule or functional variant thereof, said miRNA being upregulated in a body fluid or element thereof upon activation of said body fluid or element thereof; for the treatment of an indication selected from the list consisting of a disease or disorder associated with inflammation, a disease of the immune system, such as undesirable activation of the immune system, cancer or other indications associated with abnormal cell growth or cell division, such as leukaemia, chronic inflammation, paradontosis, abortus habitualis, colitis ulcerosa, polymyalgia rheumatica, whiplash-associated disorders, endometriosis, such as adenomyosis, Parkinson's disease, Alzheimer's disease, dementia, diabetes, such as diabetes I, AIDS/HIV, osteoporosis, psoriasis, and wound healing, conditions in the reproduction system, such as low sperm production, inflammatory or degenerative conditions in the gametes or their derivatives, development of sertoli cell only syndrome, and abortions of fetus in human and animals.

Further to this the compositions according to the present invention may have an effect on enhancing primordial follicular development in the ovary in conditions such as degenerative diseases in the ovary, chromosome aberrations or inflammatory conditions in the peritoneal cavity.

In a third aspect the present invention relates to a method for the preparation of a composition comprising a therapeutically effective amount of one or more miRNA molecule or functional variant thereof, said miRNA being upregulated in a body fluid or element thereof upon activation of said body fluid or element thereof, the method comprising the steps of
a) Collecting said body fluid or element thereof from a mammal;
b) Incubating the collected body fluid or element thereof in contact with an increased surface area;
c) Collecting said body fluid produced after step b) and optionally purifying said miRNA.

In some embodiments, the body fluid or element thereof is incubated under step b) for more than 24 hours, such as more than 48 hours, such as for more than 60 hours, 72 hours, 84 hours, 96 hours, 120 hours, or 150 hours.

In a further aspect the present invention relates to a method for the preparation of a composition comprising a therapeutically effective amount of one or more miRNA molecule or functional variant thereof, said miRNA being upregulated in a body fluid or element thereof upon activation of said body fluid or element thereof, the method comprising the steps of
a) Collecting said body fluid or element thereof from a mammal;
b) Incubating the collected body fluid or element thereof in contact with an increased surface area;
c) Identifying one or more miRNA upregulated in said body fluid or element thereof;
d) Providing said one or more miRNA molecule identified in step c) in isolated form and adding them to said composition.

In a further aspect the present invention relates to a kit of parts comprising
a) a device for preparing a composition comprising a therapeutically effective amount of one or more miRNA molecule or functional variant thereof, said miRNA being upregulated in a body fluid or element thereof upon activation of said body fluid or element thereof, the device comprising a vessel optionally with an inductor; and
b) instructions for use according to the methods of the invention; and
c) optionally a preparation of magnetic nanoparticles, such as polyethyleneimine (PEI) coated iron magnetic nanoparticles.

In some embodiments the vessel has a wall structure formed continuously about an internal space and an entry point provided in a top end of the wall for injecting the body fluid or element thereof into the internal space.

In a further aspect the present invention relates to a method for the treatment or for alleviating the symptoms of a disease or disorder associated with inflammation, a disease of the immune system, such as undesirable activation of the immune system and/or cancer or other indications associated with abnormal cell growth or cell division, the method comprising administering a composition comprising a therapeutically effective amount of one or more miRNA molecule or functional variant thereof, said miRNA being upregulated in a body fluid or element thereof upon activation of said body fluid or element thereof to a subject in need of said treatment.

In some embodiments, the therapeutic method according to the invention further comprises a step of positioning in vivo of a magnet in or close to the site of the disease, such as in or around a tumour after administering of said composition comprising a preparation of magnetic nanoparticles to which the miRNA molecules are bound.

In a further aspect the present invention relates to a method for the treatment for alleviating the symptoms of diseases of autoimmune disorders or inappropriate cell growth or responses, using a virus vector to introduce the mirRNA into the body.

In a further aspect the present invention relates to a device suitable for the methods of the present invention consisting of a 60 ml container suitable for centrifugation comprising two rubber ports for injection and a small hole for pressure equalization, the container being with or without 2-25 gram of glass beads, 1-8 mm, such as 4 mm. Other means than beads for increasing the surface area may be used.

Other potentially suitable devices are described in any one of EP0740964, EP1638691, WO2008097230, EP1093390, or EP1549552, the device being prefilled in the chamber for collection of supernatant with beads to stimulate the production of miRNA, or the chamber for collection of supernatant being provided with a surface structure which stimulates the production of miRNA.

In a further aspect the present invention relates to method for the activation of a blood preparation, wherein the blood preparation is activated in a device as described herein or potentially in any one of EP0740964, EP1638691, WO2008097230, EP1093390, or EP1549552, the device being prefilled in the chamber for collection of supernatant with beads to stimulate the production of miRNA, or the chamber for collection of supernatant being provided with a surface structure which stimulates the production of miRNA.

DETAILED DISCLOSURE OF THE INVENTION

The present inventors have found that upon activation, such as stimulation on a surface of body fluids containing monocytes certain miRNAs are upregulated. The present inventors have also found that such activated body fluid may be used in the treatment of a wide range of indications, such as diseases or disorders associated with inflammation, a disease of the immune system, such as undesirable activation of the immune system, cancer or other indications associated with abnormal cell growth or cell division.

Accordingly the present inventors have realised that compositions may be prepared to contain therapeutically effective miRNA molecules or functional variants thereof.

In some embodiments the miRNA is selected from the list consisting of hsa-let-7a, hsa-let-7a-1, hsa-let-7a-2, hsa-let-7a-3, hsa-let-7b, hsa-let-7b*, hsa-let-7c, hsa-let-7d, hsa-let-7d*, hsa-let-7e, hsa-let-7e*, hsa-let-7f, hsa-let-7f-1, hsa-let-7f-2, hsa-let-7g, hsa-let-7l, hsa-miR-1, hsa-miR-1-2, hsa-miR-100, hsa-miR-100-1, hsa-miR-100-2, hsa-miR-101, hsa-miR-101-1, hsa-miR-101a, hsa-miR-101b-2, hsa-miR-102, hsa-miR-103, hsa-miR-103-1, hsa-miR-103-2, hsa-miR-104, hsa-miR-105, hsa-miR-106a, hsa-miR-106a-1, hsa-miR-106b, hsa-miR-106b-1, hsa-miR-107, hsa-miR-10a, hsa-miR-10b, hsa-miR-122a, hsa-miR-1228*, hsa-miR-123, hsa-miR-124a, hsa-miR-124a-1, hsa-miR-124a-2, hsa-miR-124a-3, hsa-miR-125a, hsa-miR-125b, hsa-miR-125b-1, hsa-miR-125b-2, hsa-miR-126, hsa-miR-126-5p, hsa-miR-126*, hsa-miR-127, hsa-miR-128a, hsa-miR-128b, hsa-miR-129, hsa-miR-129-1, hsa-miR-129-2, hsa-miR-130, hsa-miR-130a, hsa-miR-130a-1, hsa-miR-130b, hsa-miR-130b-1, hsa-miR-132, hsa-miR-133a, hsa-miR-133b, hsa-miR-134, hsa-miR-135a, hsa-miR-135b, hsa-miR-136, hsa-miR-137, hsa-miR-138, hsa-miR-138-1, hsa-miR-138-2, hsa-miR-139, hsa-miR-139-5p, hsa-miR-140, hsa-miR-140*, hsa-miR-141, hsa-miR-142-3p, hsa-miR-142-5p, hsa-miR-143, hsa-miR-144, hsa-miR-144*, hsa-miR-145, hsa-miR-146a, hsa-miR-146a*, hsa-miR-146b, hsa-miR-147, hsa-miR-148a, hsa-miR-148b, hsa-miR-149, hsa-miR-15, hsa-miR-150, hsa-miR-151, hsa-miR-151*, hsa-miR-152, hsa-miR-153, hsa-miR-154, hsa-miR-154*, hsa-miR-155, hsa-miR-15a, hsa-miR-15a-2, hsa-miR-15b, hsa-miR-16, hsa-miR-16-1, hsa-miR-16-2, hsa-miR-16a, hsa-miR-164, hsa-miR-170, hsa-miR-172a-2, hsa-miR-17, hsa-miR-17-3p, hsa-miR-17-5p, hsa-miR-17-92, hsa-miR-18, hsa-miR-18a, hsa-miR-18b, hsa-miR-18a*, hsa-miR-181a, hsa-miR-181a-1, hsa-miR-181a-2, hsa-miR-181a*, hsa-miR-181a-1*, hsa-miR-181b, hsa-miR-181b-1, hsa-miR-181b-2, hsa-miR-181c, hsa-miR-181d, hsa-miR-182, hsa-miR-182*, hsa-miR-183, hsa-miR-184, hsa-miR-185, hsa-miR-186, hsa-miR-188, hsa-miR-189, hsa-miR-190, hsa-miR-191, hsa-miR-192, hsa-miR-192-1, hsa-miR-192-2, hsa-miR-192-3, hsa-miR-193a, hsa-miR-193b, hsa-miR-194, hsa-miR-195, hsa-miR-195*, hsa-miR-196a, hsa-miR-196a-2, hsa-miR-196b, hsa-miR-197, hsa-miR-198, hsa-miR-199a, hsa-miR-199a-1, hsa-miR-199a-1-5p, hsa-miR-199a-2, hsa-miR-199a-2-5p, hsa-miR-199a-3p, hsa-miR-199b, hsa-miR-199b-5p, hsa-miR-19a, hsa-miR-19b, hsa-miR-19b-1, hsa-miR-19b-2, hsa-miR-200a, hsa-miR-200b, hsa-miR-200c, hsa-miR-202, hsa-miR-203, hsa-miR-204, hsa-miR-205, hsa-miR-206, hsa-miR-207, hsa-miR-208, hsa-miR-20a, hsa-miR-20b, hsa-miR-21, hsa-miR-210, hsa-miR-211, hsa-miR-212, hsa-miR-213, hsa-miR-214, hsa-miR-215, hsa-miR-216, hsa-miR-217, hsa-miR-218, hsa-miR-218-2, hsa-miR-219, hsa-miR-219-1, hsa-miR-22, hsa-miR-220, hsa-miR-221, hsa-miR-222, hsa-miR-223, hsa-miR-224, hsa-miR-23a, hsa-miR-23b, hsa-miR-24, hsa-miR-24-1, hsa-miR-24-2, hsa-miR-25, hsa-miR-26a, hsa-miR-26a-1, hsa-miR-26a-2, hsa-miR-26b, hsa-miR-27a, hsa-miR-27b, hsa-miR-28, hsa-miR-296, hsa-miR-298, hsa-miR-299-3p, hsa-miR-299-5p, hsa-miR-29a, hsa-miR-29a-2, hsa-miR-29b, hsa-miR-29b-1, hsa-miR-29b-2, hsa-miR-29c, hsa-miR-301, hsa-miR-302, hsa-miR-302a, hsa-miR-302b, hsa-miR-302b*, hsa-miR-302c, hsa-miR-302c*, hsa-miR-302d, hsa-miR-30a, hsa-miR-30a-3p, hsa-miR-30a-5p, hsa-miR-30b, hsa-miR-30b*, hsa-miR-30c, hsa-miR-30c-1, hsa-miR-30d, hsa-miR-30e, hsa-miR-30e*, hsa-miR-30e-5p, hsa-miR-31, hsa-miR-32, hsa-miR-32*, hsa-miR-320, hsa-miR-320-2, hsa-miR-320a, hsa-miR-323, hsa-miR-324-3p, hsa-miR-324-5p, hsa-miR-325, hsa-miR-326, hsa-miR-328, hsa-miR-328-1, hsa-miR-33, hsa-miR-330, hsa-miR-331, hsa-miR-335, hsa-miR-337, hsa-miR-337-3p, hsa-miR-338, hsa-miR-338-5p, hsa-miR-339, hsa-miR-339-5p, hsa-miR-34a*, hsa-miR-340, hsa-miR-340*, hsa-miR-341, hsa-miR-342, hsa-miR-342-3p, hsa-miR-345, hsa-miR-346, hsa-miR-347, hsa-miR-34a, hsa-miR-34b, hsa-miR-34c, hsa-miR-351, hsa-miR-352, hsa-miR-361, hsa-miR-362, hsa-miR-363, hsa-miR-355, hsa-miR-365, hsa-miR-367, hsa-miR-368, hsa-miR-369-5p, hsa-miR-370, hsa-miR-371, hsa-miR-372, hsa-miR-373, hsa-miR-373*, hsa-miR-374, hsa-miR-375, hsa-miR-376a, hsa-miR-376b, hsa-miR-377, hsa-miR-378, hsa-miR-379, hsa-miR-381, hsa-miR-382, hsa-miR-383, hsa-miR-409-3p, hsa-miR-419, hsa-miR-422a, hsa-miR-422b, hsa-miR-423, hsa-miR-424, hsa-miR-429, hsa-miR-431, hsa-miR-432, hsa-miR-432*, hsa-miR-433, hsa-miR-449a, hsa-miR-451, hsa-miR-452, hsa-miR-483, hsa-miR-483-3p, hsa-miR-484, hsa-miR-485-5p, hsa-miR-485-3p, hsa-miR-486, hsa-miR-487b, hsa-miR-451, hsa-miR-452, hsa-miR-452*, hsa-miR-491, hsa-miR-492, hsa-miR-493-3p, hsa-miR-493-5p, hsa-miR-494, hsa-miR-495, hsa-miR-497, hsa-miR-498, hsa-miR-5, hsa-miR-501, hsa-miR-503, hsa-miR-508, hsa-miR-509, hsa-miR-510, hsa-miR-511, hsa-miR-512-5p, hsa-miR-513, hsa-miR-513-1, hsa-miR-513-2, hsa-miR-515-3p, hsa-miR-516-5p, hsa-miR-516-3p, hsa-miR-518a-2*, hsa-miR-518b, hsa-miR-518c*, hsa-miR-519a, hsa-miR-519d, hsa-miR-520c, hsa-miR-521, hsa-miR-524*, hsa-miR-525*, hsa-miR-532-5p, hsa-miR-539, hsa-miR-542-3p, hsa-miR-542-5p, hsa-miR-550, hsa-miR-551a, hsa-miR-561, hsa-miR-563, hsa-miR-565, hsa-miR-572, hsa-miR-582, hsa-miR-584, hsa-miR-594, hsa-miR-595, hsa-miR-598, hsa-miR-600, hsa-miR-601, hsa-miR-602, hsa-miR-605, hsa-miR-608, hsa-miR-611, hsa-miR-612, hsa-miR-615, hsa-miR-615-3p, hsa-miR-622, hsa-miR-627, hsa-miR-628, hsa-miR-635, hsa-miR-637, hsa-miR-638, hsa-miR-642, hsa-miR-648, hsa-miR-652, hsa-miR-654, hsa-miR-657, hsa-miR-658, hsa-miR-659, hsa-miR-662, hsa-miR-663, hsa-miR-7, hsa-miR-7-1, hsa-miR-7-1*, hsa-miR-7-2, hsa-miR-7-3, hsa-miR-708, hsa-miR-765, hsa-miR-769-3p, hsa-miR-802, hsa-miR-885-3p, hsa-miR-9, hsa-miR-9-1, hsa-miR-9-3, hsa-miR-9*, hsa-miR-9-3p, hsa-miR-92, hsa-miR-92-1, hsa-miR-92-2, hsa-miR-9-2, hsa-miR-92, hsa-miR-92a, hsa-miR-93, hsa-miR-95, hsa-miR-96, hsa-miR-98, hsa-miR-99a, and hsa-miR-99b and variant thereof.

In some embodiments the miRNA is selected from the list consisting of hsa-Let-7a, hsa-Let-7b, hsa-Let-7b*, hsa-Let-7c, hsa-Let-7d, hsa-Let-7d*, hsa-Let-7e, hsa-Let-7f, hsa-Let-7f*, hsa-Let-7g, hsa-Let-7g*, hsa-Let-7i, hsa-miR-103, hsa-miR-106A, hsa-miR-106B, hsa-miR-107, hsa-miR-125A, hsa-miR-125B, hsa-miR-126, hsa-miR-128, hsa-miR-130A, hsa-miR-130B, hsa-miR-140-3P, hsa-miR-140-5P, hsa-miR-142-3P, hsa-miR-142-5P, hsa-miR-143, hsa-miR-144, hsa-miR-146A, hsa-miR-148A, hsa-miR-148B, hsa-miR-150, hsa-miR-151-3P, hsa-miR-151-5P, hsa-miR-152, hsa-miR-15A, hsa-miR-15B, hsa-miR-16, hsa-miR-15B*, hsa-miR-17, hsa-miR-181A, hsa-miR-185, hsa-miR-186, hsa-miR-18A, hsa-miR-18A*, hsa-miR-18B, hsa-miR-192, hsa-miR-191, hsa-miR-194, hsa-miR-197, hsa-miR-1979, hsa-miR-19A, hsa-miR-19B, hsa-miR-20A, hsa-miR-20B, hsa-miR- 21, hsa-miR-205, hsa-miR-210, hsa-miR-215, hsa-miR-22, hsa-miR-22*, hsa-miR-221, hsa-miR-222, hsa-miR-223, hsa-miR-223*, hsa-miR-23A, hsa-miR-23B, hsa-miR-24, hsa-miR-25, hsa-miR-26A, hsa-miR-26B, hsa-miR-27A, hsa-miR-27B, hsa-miR-28-5P, hsa-miR-29A, hsa-miR-29B, hsa-miR-29C, hsa-miR-30A, hsa-miR-301A, hsa-miR-30B, hsa-miR-30C, hsa-miR-30D, hsa-miR-30E, hsa-miR-320A, hsa-miR-320B, hsa-miR-324-3P, hsa-miR-326, hsa-miR-328, hsa-miR-338-3P, hsa-miR-342-3P, hsa-miR-339-5P, hsa-miR-33A, hsa-miR-342-3P, hsa-miR-365, hsa-miR-378, hsa-miR-423-3P, hsa-miR-423-5P, hsa-miR-424, hsa-miR-425, hsa-miR-451, hsa-miR-484, hsa-miR-486-5P, hsa-miR-505, hsa-miR-502-3P, hsa-miR-590-5P, hsa-miR-628-3P, hsa-miR-652, hsa-miR-660, hsa-miR-720, hsa-miR-92A, hsa-miR-92B, hsa-miR-93, hsa-miR-93*, hsa-miR-99A, hsa-miR-99B, hsa-miR-103-2*, hsa-miR-106B*, hsa-miR-133A, hsa-miR-133B, hsa-miR-338-3P, hsa-miR-340, hsa-miR-34A, hsa-miR-34B, hsa-miR-376A, hsa-miR-532-3P, hsa-miR-125A-5P, hsa-miR-154, hsa-miR-196B, hsa-miR-1979, hsa-miR-326, hsa-miR-425*, hsa-miR-127-3P, hsa-miR-1537, hsa-miR-183, hsa-miR-29B-2*, hsa-miR-339-3P, hsa-miR-551A, hsa-miR-629, hsa-miR-766, hsa-miR-2110, hsa-miR-361-3P, hsa-miR-501-5P, hsa-miR-940, hsa-miR-1249, hsa-miR-132, hsa-miR-1538, hsa-miR-149, hsa-miR-125a-5P, hsa-miR-132, hsa-miR-155, hsa-miR-182, hsa-miR-324-5P, hsa-miR-331-3P, hsa-miR-335, hsa-miR-374b, and hsa-miR-532-5P, and variant thereof.

In some embodiments, the miRNA is a member of the Let-7 family, or variants thereof.

In some embodiments, the composition according to the invention further comprises a miRNA selected from the group consisting of hsa-miR-7, hsa-Let-7a, hsa-Let-7b, hsa-Let-7b*, hsa-Let-7c, hsa-Let-7d, hsa-Let-7d*, hsa-Let-7e, hsa-Let-7f, hsa-Let-7f*, hsa-Let-7g, hsa-Let-7g*, hsa-Let-7i, hsa-miR-103, hsa-miR-106A, hsa-miR-106B, hsa-miR-107, hsa-miR-125A, hsa-miR-125B, hsa-miR-126, hsa-miR-128, hsa-miR-130A, hsa-miR-130B, hsa-miR-140-3P, hsa-miR-140-5P, hsa-miR-142-3P, hsa-miR-142-5P, hsa-miR-143, hsa-miR-144, hsa-miR-146A, hsa-miR-148A, hsa-miR-148B, hsa-miR-150, hsa-miR-151-3P, hsa-miR-151-5P, hsa-miR-152, hsa-miR-15A, hsa-miR-15B, hsa-miR-16, hsa-miR-15B*, hsa-miR-17, hsa-miR-181A, hsa-miR-185, hsa-miR-186, hsa-miR-18A, hsa-miR-18A*, hsa-miR-18B, hsa-miR-192, hsa-miR-191, hsa-miR-194, hsa-miR-197, hsa-miR-1979, hsa-miR-19A, hsa-miR-19B, hsa-miR-20A, hsa-miR-20B, hsa-miR-21, hsa-miR-205, hsa-miR-210, hsa-miR-215, hsa-miR-22, hsa-miR-22*, hsa-miR-221, hsa-miR-222, hsa-miR-223, hsa-miR-223*, hsa-miR-23A, hsa-miR-23B, hsa-miR-24, hsa-miR-25, hsa-miR-26A, hsa-miR-26B, hsa-miR-27A, hsa-miR-27B, hsa-miR-28-5P, hsa-miR-29A, hsa-miR-29B, hsa-miR-29C, hsa-miR-30A, hsa-miR-301A, hsa-miR-30B, hsa-miR-30C, hsa-miR-30D, hsa-miR-30E, hsa-miR-320A, hsa-miR-320B, hsa-miR-324-3P, hsa-miR-326, hsa-miR-328, hsa-miR-338-3P, hsa-miR-342-3P, hsa-miR-339-5P, hsa-miR-33A, hsa-miR-342-3P, hsa-miR-365, hsa-miR-378, hsa-miR-423-3P, hsa-miR-423-5P, hsa-miR-424, hsa-miR-425, hsa-miR-451, hsa-miR-484, hsa-miR-486-5P, hsa-miR-505, hsa-miR-502-3P, hsa-miR-590-5P, hsa-miR-628-3P, hsa-miR-652, hsa-miR-660, hsa-miR-720, hsa-miR-92A, hsa-miR-92B, hsa-miR-93, hsa-miR-93*, hsa-miR-99A, hsa-miR-99B, hsa-miR-103-2*, hsa-miR-106B*, hsa-miR-133A, hsa-miR-133B, hsa-miR-338-3P, hsa-miR-340, hsa-miR-34A, hsa-miR-34B, hsa-miR-376A, hsa-miR-532-3P, hsa-miR-125A-5P, hsa-miR-154, hsa-miR-196B, hsa-miR-1979, hsa-miR-326, hsa-miR-425*, hsa-miR-127-3P, hsa-miR-1537, hsa-miR-183, hsa-miR-29B-2*, hsa-miR-339-3P, hsa-miR-551A, hsa-miR-629, hsa-miR-766, hsa-miR-2110, hsa-miR-361-3P, hsa-miR-501-5P, hsa-miR-940, hsa-miR-1249, hsa-miR-132, hsa-miR-1538, and hsa-miR-149, hsa-miR-125a-5P, hsa-miR-132, hsa-miR-155, hsa-miR-182, hsa-miR-324-5P, hsa-miR-331-3P, hsa-miR-335, hsa-miR-374b, and hsa-miR-532-5P, hsa-miR-320a, hsa-miR-130a, hsa-miR-320c, hsa-miR-628-3p, hsa-miR-637, hsa-miR-320b, hsa-miR-129-5p, hsa-miR-943, hsa-miR-185*, hsa-miR-340*, hsa-miR-744, hsa-miR-638, hsa-miR-585, hsa-miR-26b, hsa-miR-485-3p, hsa-miR-103, hsa-miR-146b-5p, hsa-miR-642, hsa-miR-146a, hsa-let-7a, hsa-let-7f, hsa-miR-200b*, hsa-miR-320d, hsa-let-7d, hsa-miR-1282, hsa-miR-124, hsa-miR-602, hsa-let-7g, hsa-miR-221, hsa-miR-25*, hsa-miR-1184, hsa-miR-663, hsa-miR-93, hsa-miR-30b*, hsa-miR-124*, hsa-miR-22, hsa-miR-1281, hsa-miR-1237, hsa-miR-34b, hsa-miR-1290, hsa-miR-193b*, hsa-miR-526b, hsa-miR-622, hsa-miR-191, hsa-miR-142-3p, hsa-miR-92a, hsa-miR-1280, hsa-miR-1236, hsa-miR-30c, hsa-miR-877*, hsa-miR-548n, hsa-miR-1249, hsa-let-7i, hsa-miR-1224-3p, hsa-miR-17, hsa-miR-300, hsa-miR-193a-5p, hsa-let-7d*, hsa-miR-24, hsa-miR-518c*, hsa-miR-222, hsa-miR-664, hsa-miR-130b, hsa-miR-625*, hsa-miR-593, hsa-miR-885-5p, hsa-miR-505*, hsa-miR-491-3p, hsa-miR-421, hsa-miR-7, hsa-miR-106a, hsa-miR-99b*, hsa-miR-1300, hsa-miR-92b, hsa-miR-30d, hsa-miR-720, hsa-miR-1260, hsa-miR-425, hsa-miR-939, hsa-miR-30a, hsa-miR-30e, hsa-miR-654-5p, hsa-miR-509-5p, hsa-miR-1826 and variants thereof.

Definitions

As used herein, the term "miRNA" or "miR" or "microRNA" means a non-coding RNA between 17 and 25 nucleobases in length which hybridizes to and regulates the expression of a coding RNA. A 17-25 nucleotide miRNA molecule can be obtained from a miR precursor through natural processing routes (e.g., using intact cells or cell lysates) or by synthetic processing routes (e.g., using isolated processing enzymes, such as isolated Dicer, Argonaut, or RNAase III). It is understood that the 17-25 nucleotide RNA molecule can also be produced directly by biological or chemical syntheses, without having been processed from a miR precursor.

As used herein the term "miRNA molecule" refers to any nucleic acid molecule representing a miRNA. Included within this definition are natural miRNA molecules, pre-miRNA, pri-miRNA, miRNA molecules identical in nucleic acid sequence to the natural forms as well as nucleic acid sequences, wherein one or more nucleic acids has been replaced or is represented by one or more DNA nucleotide and/or nucleic acid analogue. miRNA molecules is in the present specification occasionally referred to as a nucleic acid molecule encoding a miRNA or simply nucleic acid molecule.

As used herein, the term "miR precursor," "pre-miRNA" or "pre-miR" means a non-coding RNA having a hairpin structure, which contains a miRNA. In certain embodiments, a pre-miRNA is the product of cleavage of a primary mi-RNA transcript, or "pri-miR" by the double-stranded RNA-specific ribonuclease known as Drosha, but a pre-miRNAs can also be produced directly by biological or chemical synthesis without having been processed from a pri-miR.

The term "body fluid or element thereof" refers to any fluid or elements derived thereof that may be obtained from the body of a mammal. Included within this definition are cerebrospinal fluids, blood, such as blood from the circulatory system or from the umbilical cord, serum, lymph fluid, plasma, pleura exudates, peritoneal exudates, bone marrow exudates, extracellular fluids, fluids from the joints, amniotic fluids. Included within this definition are also cells, such hematopoietic stem cells or in vitro cell cultures, such as a monocyte cell cultures, as well as exosomes or other substructures that may be derived from a body fluid.

The term "conditioned cell culture medium" as used herein refers to a medium, such as a growth medium wherein cells have been cultured for a period of time, such as by in vitro cultivation. The period of time for culturing may be 1, 2, 4, 8, 16, 24, 48, 72 hours or as long as the cells are viable and stabile.

In a preferred embodiment, the body fluid according to the invention comprises leukocytes, such as monocytes and dendritic cells.

Bone marrow exudates may be obtained by bone marrow aspiration, wherein an amount of bone marrow (such as from the hip) is removed through a needle. The needle is placed through the top layer of bone and a liquid sample containing bone marrow cells is obtained by aspirating it into a syringe. The bone marrow exudates may further be centrifuged to obtain a fraction containing blood cells.

In some embodiments the body fluid is blood, such as peripheral blood or any component derived from blood, such as monocytes.

The terms "activation", "activated" or "conditioned" as used herein refers to the treatment of a body fluid or element thereof in vitro or in vivo, for a period of time in a container comprising a surface, such as a surface that is able to trigger an immunological response in the leukocytes, such as monocytes or dendritic cells of a blood preparation. In some embodiment whole blood is activated by exposure to an enhancing agent, or by stimulation to express an enhancing agent.

The term "autologous" as used herein refers to a preparation of a composition that are administered to the same individual as they come from. In a preferred embodiment, the composition is autologous to the mammal in need of said treatment.

As used herein, the phrase "alleviating the symptoms" means a lessening of severity of at least one indicator of a condition or disease. In certain embodiments, alleviating the symptoms includes a delay or slowing in the progression of one or more indicators of a condition or disease. The severity of indicators may be determined by subjective or objective measures which are known to those skilled in the art.

In the present context, the term "treatment" is meant to include both prevention of an expected condition associated with inflammation, a disease of the immune system, such as undesirable activation of the immune system, cancer or other indications associated with abnormal cell growth or cell division.

Prophylactic administration of the one or more miRNA molecule or functional variant thereof according to the invention is thus included in the term "treatment".

The term "subject" as used herein is intended to mean any animal, in particular mammals, such as humans, and may, where appropriate, be used interchangeably with the term "patient".

As used herein, the term "cancer" includes, but is not limited to, solid tumors and blood borne tumors, including leukemia and lymphoma. The term cancer refers to diseases of the skin, tissues, organs, bone, cartilage, blood and vessels. The term "cancer" further encompasses primary and metastatic cancers.

MicroRNA

The present invention is directed to compositions and methods related to the use of miRNA molecules in the treatment of an indication selected from the list consisting of a disease or disorder associated with inflammation, a disease of the immune system, such as undesirable activation of the immune system, cancer or other indications associated with abnormal cell growth or cell division.

It is well known in the art that modifications can be made to the sequence of a miRNA or a pre-miRNA or pri-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments the "functional variants" refers to a miRNA that vary by one or two nucleotides, such as one or two substitutions, additions, deletions or combinations thereof. In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant may is capable of hybridizing to one or more target sequences of the miRNA.

It is understood that any nucleobase sequence set forth herein are independent of any modification to a sugar moiety, an internucleoside linkage, or a nucleobase. It is further understood that a nucleobase sequence comprising U's also encompasses the same nucleobase sequence wherein "U" is replaced by "T at one or more positions having "U." Conversely, it is understood that a nucleobase sequence comprising T's also encompasses the same nucleobase sequence wherein "T; is replaced by "U at one or more positions having "T".

Nucleobase sequences miRNAs and their corresponding stem-loop sequences described herein may be found in miR-Base, an online searchable database of miRNA sequences and annotation, found at http://microrna.sanger.ac.uk/. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

The term "Let-7 miRNA family" refers to the collection of miRNA including the species of hsa-let-7a-1, hsa-let-7a-2, hsa-let-7a-3, hsa-let-7b, hsa-let-7c, hsa-let-7d, hsa-let-7e, hsa-let-7f-1, hsa-let-7f-2, hsa-let-7g, and hsa-let-7i.

The present invention pertains to pharmaceutical compositions containing nucleic acid molecules. As used herein, the term "nucleic acid molecule" is intended to include DNA molecules and RNA molecules and analogs of the DNA or RNA generated using nucleotide analogs. The nucleic acid molecule can be single-stranded or double-stranded, such as in the form of Small interfering RNA (siRNA) or double stranded miRNA (dsmiRNA), and may be generated using purified enzymes or by chemical synthesis. They may be crude or purified. The term "miRNA," unless otherwise indicated, refers to the mature miRNA sequence.

In specific embodiments, a nucleic acid molecule of the present invention comprises a nucleotide sequence which is at least about 60%, 65%, 70%, 75%, 80%, 85%, 90%, 91%, 92%, 93%, 94%, 95%, 96%, 97%, 98%, 99% or more identical to the entire length of the miRNA, or a portion of any of these nucleotide sequences.

In specific embodiments, a nucleic acid molecule of the present invention comprises a nucleotide sequence which is less than about 100 nucleotides in length, such as less than about 80 nucleotides in length, such as less than about 60 nucleotides in length, such as less than about 40 nucleotides in length, such as less than about 30 nucleotides in length, such as less than about 25 nucleotides in length, such as less than about 23 nucleotides in length, such as less than about 21 nucleotides in length, such as less than about 19 nucleotides in length.

In specific embodiments, a nucleic acid molecule of the present invention comprises a nucleotide sequence, which is at least about 19 nucleotides, such as at least about 21 nucleotides, such as at least about 23 nucleotides, such as at least about 25 nucleotides, such as at least about 30 nucleotides, such as at least about 40 nucleotides, such as at least about 50 nucleotides, such as at least about 50 nucleotides, such as at least about 60 nucleotides, such as at least about 80 nucleotides, such as at least about 100 nucleotides in length.

A nucleic acid sequence can be RNA or DNA, and can be single or double stranded, and can be selected from a group comprising: RNA nucleotides, DNA nucleotides, and nucleic acid analogues; for example peptide-nucleic acid (PNA), pseudo-complementary PNA (pc-PNA), locked nucleic acid (LNA), etc.

Medical Conditions

Diseases or disorders that may be treated according to the methods of the invention may be a cancer or other indication associated with malignant or abnormal cell growth or cell division, such as one selected from the list consisting of acute lymphoblastic leukemia (ALL), acute myeloid leukemia (AML), acute promyelocytic leukemia (APL), adenoma, adrenocortical carcinoma, alcoholic liver disease (ALD), Alzheimer's disease, anaplastic thyroid carcinoma (ATC), anxiety disorder, asthma, autism spectrum disorder (ASD), B-cell chronic lymphocytic leukemia, B-cell lymphoma, Becker muscular dystrophy (BMD), bladder cancer, breast cancer, Burkitt lymphoma, cardiac hypertrophy, cardiomyopathy, Cerebellar neurodegeneration, cervical cancer, cholangiocarcinoma, chronic lymphocytic leukemia (CLL), chronic myeloid leukemia (CML), chronic pancreatitis, colorectal cancer, congenital heart disease, coronary artery disease, Cowden Syndrome, dermatomyositis (DM), Diabetic Nephropathy, diarrhea predominant irritable bowel syndrome (IBS-D), diffuse large B-cell lymphoma (DLBCL), Down syndrome (DS), Duchenne muscular dystrophy (DMD), endometrial cancer, Endometriosis, Sarcoids, epithelial ovarian cancer (EOC), esophageal cancer, facioscapulohumeral muscular dystrophy (FSHD), follicular lymphoma (FL), follicular thyroid carcinoma (FTC), frontotemporal dementia, gastric cancer (stomach cancer), glioblastoma, glioblastoma multiforme (GBM), glioma, glomerular disease, Glomerulosclerosis, hamartoma, HBV-related cirrhosis, HCV infection, head and neck cancer, head and neck squamous cell carcinoma (HNSCC), hearing loss, heart failure, hepatocellular carcinoma (HCC), Hodgkin's lymphoma, homozygous sickle cell disease (HbSS), Huntington's disease (HD), Hypertension, Inclusion body myositis (IBM), Insulinoma, kidney cancer, laryngeal carcinoma, limb-girdle muscular dystrophies types 2A (LGMD2A), lipoma, lung cancer, lymphoproliferative disease, malignant lymphoma, malignant melanoma, Malignant mesothelioma (MM), mantle cell lymphoma (MCL), medulloblastoma, melanoma, melanoma, metabolic disease, miyoshi myopathy (MM), multiple myeloma (MM), MYC-rearranged lymphoma, myeloproliferative disorder, myoma, nasopharyngeal carcinoma (NPC), nemaline myopathy (NM), Nephritis, neuroblastoma (NB), neutrophiliais_obsolete, non-small cell lung cancer (NSCLC), Obesity, Oral Carcinoma, Oral Carcinoma, Oral Squamous Cell Carcinoma (OSCC), ovarian cancer (OC), pancreatic cancer, pancreatic ductal adenocarcinoma (PDAC), papillary thyroid carcinoma (PTC), Parkinson's disease, PFV-1 infection, pituitary adenoma, Polycystic Kidney Disease, Polycystic liver disease, polycythemia vera (PV) is_obsolete, polymyositis (PM), primary biliary cirrhosis (PBC), prostate cancer, psoriasis, pulmonary hypertension, recurrent ovarian cancer, renal clear cell carcinoma, retinitis pigmentosa (RP), retinoblastoma, rhabdomyosarcoma, sarcoma, schizophrenia, serous ovarian cancer, skin disease, Spinocerebellar ataxia, squamous carcinoma, T-cell leukemia, teratocarcinoma, testicular germ cell tumor, thalassemia, thyroid cancer, tongue squamous cell carcinoma, tourette's syndrome, type 2 diabetes, ulcerative colitis (UC), uterine leiomyoma (ULM), uveal melanoma, vascular disease, vesicular stomatitis, and Waldenstrom Macroglobulinemia (WM).

In some specific embodiments the diseases or disorders that may be treated according to the methods of the invention may is a cancer, such as melanoma, or Sarcoids.

Another disease that may be treated according to the methods of the invention is AIDS/HIV, such as the prevention of progression of HIV into AIDS.

In still other embodiments the disease that may be treated according to the methods of the invention is an indication associated with apoptosis, fat metabolism or cardiovascular diseases.

The terms "paradentosis" or "periodontitis" as used herein, refers to an inflammatory disease that affects the periodontium within the oral cavity. In some embodiments the paradentosis is associated with localized pain, erythema, swelling, loosening of teeth, and dental pockets.

The term "abortus habitualis" also known as "miscarriage" as used herein refers to the medical condition of repeated spontaneous termination of a pregnancy by the expulsion of an embryo or fetus from the uterus before the 20th week of gestation (often for no known reason). This condition is in the present embodiment also referred to unexplained infertility were the blastocysts fail to attach and implant in the endometrium due to an imbalance in factors that is corrected by this invention.

The terms "colitis ulcerosa" or "ulcerative colitis" as used herein refers to a chronic inflammatory disease of the large intestine and/or rectum. The colitis ulcerosa is often characterized by recurrent episodes of abdominal pain and fever and chills and profuse diarrhea.

The term "polymyalgia rheumatica" as used herein refers to the clinical syndrome characterized by severe aching and stiffness in the neck, shoulder girdle, and pelvic girdle, usually causing severe pain in the proximal muscle groups.

The terms "whiplash" or "whiplash-associated disorders" as used herein refers to a range of injuries to the neck caused by or related to a sudden distortion of the neck. In some embodiments the whiplash is associated with motor vehicle accidents, falls from bicycles or horses or head banging.

The term "endometriosis" as used herein refers to the general condition in women in which endometrial cells are deposited in areas outside the uterine cavity. Endometrial cells deposited in areas outside the uterus (endometriosis) may give symptoms of pelvic pain and may give rice to infertility.

In some particular embodiments, the medical condition being treated according to the present invention is endometriosis; in particular endometriosis associated with infertility, presumed infertility, or decreased fertility. In some embodiments, the condition being treated according to the present invention is unexplained infertility. In some embodiments, the patients are treated according to the present invention during or in conjunction to a procedure of In Vitro Fertilisation (IVF).

The terms "adenomyosis" or "adeomyosis" as used herein refers to the condition in women in which endometrial cells are positioned within the myometrium of the uterus outside the endometrial cavity. This may cause bleeding, pain and infertility.

In some embodiment the body fluid or element thereof may be activated in a device including but not limited to a device as disclosed in any one of international patent applications WO06007529, WO07090569, WO03080122, WO0046249, or WO9909051.

The term "inductor" or "enhancing agent" as used herein refers to any substance or compound that may be used to induce maturation or activation of the body fluid preparation used according to the invention, such in activation in antigen presenting cells (APCs). In some embodiments the inductor is a biological compound such as immunoglobulins or cancer cells that are able to induce or potentiate an immunological response in leukocytes or dendritic cells of the blood preparation.

The term "anticoagulant" as used herein refers to any substance that prevents coagulation. Included within this definition is Warfarin (Coumadin), Acenocoumarol, phenprocoumon, Phenindione, Heparin, Low molecular weight heparin, Synthetic inhibitors of factor Xa, such as Fondaparinux and Idraparinux, thrombin inhibitors, such as argatroban, lepirudin, bivalirudin, and dabigatran.

The term "Platelet-rich plasma" or "PRP", as used herein refers to a concentrated source of platelets, such as autologous platelets. PRP is known to contain and also releases (through degranulation) several growth factors (cytokines) that stimulate soft tissue healing.

In some embodiments, the body fluid used according to the invention is an activated blood serum preparation that has been mixed with platelet-rich plasma (PRP). This may be used for several types of medical disorders or conditions, such as wound healing, such as associated with surgery, tendonitis, cardiac care, cartilage regeneration, disc regeneration, and dental health.

In some non-limiting embodiments of the invention, a body fluid preparation is further activated to enhance the anti-inflammatory and/or immunosuppressive activity of the preparation.

Enhancing agents may be cytokines, cytokine antagonists, and NFkappaB antagonists, and include, but are not limited to, TGF-β, IL-10, CTLA4-Ig, sCD40-Ig, IL-4, IL-13, FasL, IL-1 receptor antagonist protein (IL-1Ra), vIL-10, sICAM-1, sICAM-3, and TRAIL. In some non-limiting embodiments, the enhancing agent is IL-1Ra, IL-10 or IL-4 or a combination thereof.

Optionally, where a specific antigen or a specific antigen source is known including but not limited to antigens derived from virus or bacteria, such specific antigen or specific antigen source (e.g., fixed or attenuated infectious agent) may be added to the culture as an enhancing agent.

In some embodiments of the invention, peripheral blood is removed from an individual, such as with a syringe, an thereafter transferred to a vessel, wherein the blood is activated by incubation in the presence of beads to stimulate the production of miRNA. Alternatively, the peripheral blood may be removed directly into a vessel comprising beads to stimulate the production of miRNA. Serum may then be collected and used according to the invention.

In still another alternative peripheral blood is removed from an individual, the buffy coat and/or serum is harvested from the blood preparation and transferred to a vessel comprising beads to stimulate the production of miRNA.

In still other alternatives peripheral blood, a preparation of bone marrow, or other preparation containing blood components is removed from an individual or obtained in other ways, transferred to a device as described herein or potentially in any one of EP0740964, EP1638691, WO2008097230, EP1093390, or EP1549552, the device being prefilled in the chamber for collection of supernatant with beads to stimulate the production of miRNA, or the wall of the chamber for collection of supernatant having a surface structure, including a clean surface, which stimulates the production of miRNA according to methods of the present invention.

Beads which may be used for this purpose include, but are not limited to, glass or plastic beads between 0.5 and 10 mm or between 0.5 and 5 mm in diameter, optionally treated with an agent, such as $CrSO_4$, which stimulates lymphocyte proliferation (Mignini et al., 2004, Preventive Med 39(4) 767-775; Rhee et al., 2002, Clin Exp Immunol 127(3):463-469). Medical grade glass beads, 4 mm in diameter may be modified by incubation in 50% $CrSO_4$. The treated or untreated beads are placed in a suitable container, such as a microtiter plate, centrifuge tube, culture tube, or syringe or other device described herein, and then sterilized (e.g. by autoclaving or gamma irradiation). Peripheral blood may in some embodiments be introduced into the bead-containing container, and then incubated, aseptically, at 37° C., optionally with 5% $CO_2$, for example for 2-200 hours, such as for 2-150 hours or 2-48 hours. Serum may then be collected from the bead/blood suspension by centrifugation, for example at 4200 rpm for 10 minutes. Typically, 30 percent of the total original peripheral blood volume may be recovered. The resulting serum containing miRNA may then be stored at −20° C.

In a related, specific, non-limiting embodiment of the invention, enhancing agents may be added to the peripheral blood sample prior to, or as an alternative to, incubation with beads. For example, 5 μg enhancing agent per ml of peripheral blood may be added.

In some, non-limiting embodiment of the invention, a blood serum preparation is prepared by collecting serum from peripheral blood, optionally incubated with beads and/or an enhancing agent, by centrifugation to remove the formed blood elements (e.g., at 3000-5000 g for 10 minutes), followed by ultracentrifugation, for example, at 100,000 g, for 1 hours. The resulting pellet may be resuspended in physiologic saline, and then preferably sterilized (e.g., by filtration through a 0.2 μm filter).

The blood may in some embodiments be treated with an anticoagulant, such as heparin or citrate.

The invention provides in a further embodiment for the incubation of the body fluid or elements thereof in the container to be carried out over a period of from 2 to 200 hours, such as 2-150 hours, such as 2-100, or 2 to 72 hours, such as 20 hours, preferably at physiological or room temperature, that is to say 20° C. to 41° C., in particular at 35-37° C.

The invention also provides in one configuration of the invention for the body fluid to be treated further after formation of the therapeutically or prophylactically active protein or compound in the body fluid, in order, for example, to remove particular constituents of the latter, for example blood plasma or blood platelets. This removal may in some embodiments of the invention be carried out by centrifugation, filtration or coagulation to remove coagulation factors and/or clotted material. In alternative embodiments of the invention the body fluid composition may be mixed with other body fluids or body fluid components.

Accordingly, in some particular embodiments, an activated body fluid composition, such an activated blood serum preparation is mixed with Platelet-rich plasma prior to administration to the patient. This is particularly suitable for use in the treatment of indications associated with joints, tendons, ligaments, and muscles, such as in the treatment of muscle pain, polymyalgia rheumatica and whiplash-associated disorders.

As discussed above the present invention relates to methods for the treatment or for alleviating the symptoms of a medical condition, compositions comprising a blood serum preparation for the preparation of a medicament for the treatment or for alleviating these symptoms, and the use of these compositions in the preparation of medicaments.

In some aspects of the invention, a blood preparation is activated in container or by alternative methods. In some alternative embodiments a blood preparation is replaced with another body fluid as described elsewhere. Accordingly, in some alternative embodiments, a container is filled with a body fluid or elements thereof, such as in vitro cell cultures, bone marrow exudates and the like, and treated by methods similar or identical to methods used for treating blood preparations. In some embodiments the body fluid is taken with a syringe directly from the patient.

In some embodiments, the buffy coat is removed from a blood preparation and activated. This may be in the presence or absence of the plasma fraction of the blood preparation. In some embodiments the buffy coat with or without plasma is incubated in the presence of a growth medium, such as during the activation on a surface or prior to said activation.

In some embodiments the compositions according to the invention further comprise micelles, vesicles or liposomes, and preferably the micelles, vesicles, liposomes comprise the miRNA.

Liposomes are typically completely closed structures comprising lipid bilayer membranes containing an encapsulated aqueous volume. Liposomes may contain many concentric lipid bilayers separated by an aqueous phase (multilamellar vesicles or MLVs), or alternatively, they may comprise a single membrane bilayer (unilamellar vesicles). The lipid bilayer is composed of two lipid monolayers having a hydrophobic "tail" region and a hydrophilic "head" region. In the membrane bilayer, the hydrophobic (nonpolar) "tails" of the lipid monolayers orient toward the centre of the bilayer, whereas the hydrophilic (polar) "heads" orient toward the aqueous phase. The lipid components that may be used in the liposomes described herein are generally described in the literature. Generally, these are phospholipids—such as phosphatidylcholine, phosphatidylethanolamine, phosphatidylglycerol, phosphatidylserine, phosphatidic acid, phosphatidylinositol and/or sphingolipids. Additional components, fore example, sterols—such as cholesterol—or other components—such as fatty acids (e.g., stearic acid, palmitic acid), dicetyl phosphate or cholesterol hemisuccinate, may be used. Moreover, the liposome membrane can also contain preservatives. The liposome membrane may also contain components, which modify their dispersion behaviour. They include, for example, PEGylated derivatives of phosphatidylethanolamine, lipids—such as GM 1—or conjugates of sugars and hydrophobic components—such as palmitic or stearic acid esters of dextran.

The basic structure of liposomes may be made by a variety of techniques known in the art.

For example, liposomes have typically been prepared using the process of Bangham et al., (1965 J. MoI. Biol., 13: 238-252), whereby lipids suspended in organic solvent are evaporated under reduced pressure to a dry film in a reaction vessel. An appropriate amount of aqueous phase is then added to the vessel and the mixture agitated. The mixture is then allowed to stand, essentially undisturbed for a time sufficient for the multilamellar vesicles to form.

Liposomes may be reproducibly prepared using a number of currently available techniques. The types of liposomes which may be produced using a number of these techniques include small unilamellar vesicles (SUVs) [See Papahadjapoulous and Miller, Biochem. Biophys. Acta., 135, p. 624-638 (1967)], reverse-phase evaporation vesicles (REV) [See U.S. Pat. No. 4,235,871 issued Nov. 25, 1980], stable plurilamellar vesicles (SPLV) [See U.S. Pat. No. 4,522,803, issued Jun. 11, 1985], and large unilamellar vesicles produced by an extrusion technique as described in copending U.S. patent application Ser. No. 622,690, filed Jun. 20, 1984, Cullis et.al., entitled "Extrusion Technique for Producing Unilamellar Vesicles". In a preferred embodiment, the liposomes are prepared using the following method. The lipids are prepared by pipetting the appropriate amount of stock solutions of, for example, CDAN, DOPE and aminoxylipid (CPA), respectively, into a round bottomed flask pre-treated with nitric acid and dimethylsilyldichlorid, evaporating the solvent, and hydrating the dry lipid film with water under heavy vortexing, to generate multilamellar liposomes.

Unilamellar liposomes may be produced by sonicating the multilamellar liposomes for 30 mins. Preferably, this is continued until a size of smaller than about 30 nm is reached.

Specific Embodiments of the Invention

In some embodiments the composition suitable for therapeutic application is used for the treatment of the same individual as where the composition derives, i.e. autologous use, such as a use in the same human being from where a blood sample has been obtained and activated.

However, the composition suitable for therapeutic application may also be derived from a genetically non-identical member of the same species, such as another human being. In this case the preparation of a body fluid or element thereof is referred to as allogeneic or homologous.

In some embodiments the composition suitable for therapeutic application derives from another species, i.e. a heterologous preparation. This may be a heterologous preparation from similar or closely related mammals.

In one preferred embodiment, the body fluid is blood, derived from the circulatory system.

In some embodiments the body fluid is a preparation of blood without significant levels of red blood cells. In some embodiments the body fluid preparation contains intact monocytes, such as significant levels to have a measurable effect of the activation.

In some embodiments, body fluid preparation is lacking significant levels of clotting factors. The "body fluid preparation" may in some embodiments contain clotting factors.

In some embodiments the miRNA used according to the invention is selected from the group consisting of hsa-miR-320a, hsa-miR-130a, hsa-miR-320c, hsa-miR-628-3p, hsa-miR-637, hsa-miR-320b, hsa-miR-129-5p, hsa-miR-943, hsa-miR-185*, hsa-miR-340*, hsa-miR-744, hsa-miR-638, hsa-miR-585, hsa-miR-26b, hsa-miR-485-3p, hsa-miR-103, hsa-miR-146b-5p, hsa-miR-642, hsa-miR-146a, hsa-let-7a, hsa-let-7f, hsa-miR-200b*, hsa-miR-320d, hsa-let-7d, hsa-miR-1282, hsa-miR-124, hsa-miR-602, hsa-let-7g, hsa-miR-221, hsa-miR-25*, hsa-miR-1184, hsa-miR-663, hsa-miR-93, hsa-miR-30b*, hsa-miR-124*, hsa-miR-22, hsa-miR-1281, hsa-miR-1237, hsa-miR-34b, hsa-miR-1290, hsa-miR-193b*, hsa-miR-526b, hsa-miR-622, hsa-miR-191, hsa-miR-142-3p, hsa-miR-92a, hsa-miR-1280, hsa-miR-1236, hsa-miR-30c, hsa-miR-877*, hsa-miR-548n, hsa-miR-1249, hsa-let-7i, hsa-miR-1224-3p, hsa-miR-17, hsa-miR-300, hsa-miR-193a-5p, hsa-let-7d*, hsa-miR-24, hsa-miR-518c*, hsa-miR-222, hsa-miR-664, hsa-miR-130b, hsa-miR-625*, hsa-miR-593, hsa-miR-885-5p, hsa-miR-505*, hsa-miR-491-3p, hsa-miR-421, hsa-miR-7, hsa-miR-106a, hsa-miR-99b*, hsa-miR-1300, hsa-miR-92b, hsa-miR-30d, hsa-miR-720, hsa-miR-1260, hsa-miR-425, hsa-miR-939, hsa-miR-30a, hsa-miR-30e, hsa-miR-654-5p, hsa-miR-509-5p, hsa-miR-1826 and variants thereof.

In some embodiments the composition according to the present invention is not derived from a blood product. In some embodiments the composition is essentially free of other blood derived components.

In some embodiments the miRNA is upregulated in a blood preparation upon activation.

In some embodiments the miRNA is upregulated in a body fluid or element thereof upon activation in a vessel optionally comprising an inductor.

In some embodiments the miRNA is upregulated upon activation on a surface selected from the group consisting of: spheres, gels, glass wool, granulated material and particles or surface structures comprising polystyrene or glass.

In some embodiments an inductor used according to the present invention is coated on a structure selected from the group consisting of: spheres, gels, glass wool, granulated material and particles or surface structures comprising polystyrene or glass. In some embodiments the inductor comprises immunoglobulin.

In some embodiments the inductor is represented by autologous, allogeneic or heterologous tumour cells, such as $10^3$-$10^7$ tumour cells per ml of the composition.

In some embodiments a specific miRNA specie is present in the composition in an amount of at least about 1000, such as at least about 5000, such as at least about $10^4$, such as at least about $5 \times 10^4$, such as at least about $10^5$, such as at least about $5 \times 10^5$, such as at least about $10^6$, such as at least about $5 \times 10^6$, such as at least about $10^7$, such as at least about $5 \times 10^7$, such as at least about $10^8$, such as at least about $5 \times 10^8$ femtogram per ml, such as up to 250 picogram per ml.

In some embodiments the total amount of miRNA is present in the composition in an amount of at least about 1000, such as at least about 5000, such as at least about $10^4$, such as at least about $5 \times 10^4$, such as at least about $10^5$, such as at least about $5 \times 10^5$, such as at least about $10^6$, such as at least about $5 \times 10^6$, such as at least about $10^7$, such as at least about $5 \times 10^7$, such as at least about $10^8$, such as at least about $5 \times 10^8$ femtogram per ml, such as up to 250 picogram per ml.

In some embodiments the one or more miRNA is present in the composition in a concentration, which is at least about 50%, such as at least about 100%, such as at least about 200%, such as at least about 300%, such as at least about 400%, such as at least about 500%, such as at least about 600%, such as at least about 700%, such as at least about 800%, higher than the concentration level of said miRNA in a composition that has not been activated.

In some embodiments the composition is derived from blood serum.

In some embodiments the composition has a normal physiological level of sodium, such as levels between 135-145 mEq/L.

In some embodiments the composition further comprises a carrier protein and/or micelles and/or vescicles and/or liposomes for the protection of miRNA from degradation by RNAases.

In some embodiments the composition according to the invention further comprises a preparation of magnetic nanoparticles, such as polyethyleneimine (PEI) coated iron magnetic nanoparticles.

In some embodiments the nucleic acid molecule used in the compositions of the invention is prepared by synthetic means.

In some embodiments the compositions comprising miRNA molecules is free from one or more serum proteins, such as serum albumin, immunoglobulins, fibrinogen, prothrombin, Alpha 1-antitrypsin, alpha2-macroglobulin and other globulins, transferrin.

In some embodiments the nucleic acid molecule is present in a measurable amount.

In some embodiments the one or more miRNA molecule present in the composition according to the invention has been upregulated to a 0.00001 to 10000 folds, such as 0.00001 to 1000 folds increase in the measurable amount during activation.

In some embodiments the nucleic acid molecule comprises affinity-enhancing nucleotide analogous, such as a peptide nucleic acid (PNA), pseudo-complementary PNA (pcPNA), locked nucleic acid (LNA) or analogue thereof.

In some embodiments the composition according to the present invention comprises at least 1-100, such as at least 2-50, such as at least 10-50 different species of a miRNA.

In some embodiments the composition further comprises a preparation of exosomes. In some embodiments the preparation of exosomes is from the same patient as from where the body fluid or elements thereof derives. In some embodiments the preparation of exosomes is produced by in vitro, such as derived from cells cultured in vitro.

Exosome preparations enriched in miRNA may be prepared using ExoQuick™ precipitation kit.

It is to be understood that the miRNA may be incorporated into or on the surface of the exosomes and may protect the miRNA from degradation.

In some embodiments the exosomes are enriched with the nucleic acid molecule according to the present invention.

In some embodiments the body fluid or element thereof according to the present invention is an in vitro cell culture, such as a monocyte cell culture.

In some embodiments the body fluid or element thereof according to the present invention is a blood serum preparation.

In some embodiments the body fluid or element thereof according to the present invention is a buffy coat preparation. In some embodiments the buffy coat preparation further comprises a plasma fraction. In some embodiments the buffy coat preparation with or without the plasma fraction is incubated together with a growth medium prior to or during the activation according to the present invention.

In some embodiments the body fluid or element thereof according to the present invention is whole blood preparation.

In some embodiments the body fluid or element thereof according to the present invention is from bone marrow exudates.

In some embodiments the activated body fluid or element thereof is further mixed with platelet-rich plasma (PRP).

In some embodiments the body fluid or element thereof according to the present invention is activated in a process that further comprises a step of treating said body fluid or element thereof with an anticoagulant, optionally followed by a step of separation, wherein the desired part of the body fluid is isolated.

In some embodiments the body fluid or element thereof according to the present invention is collected from two or more mammals, such as from more than 3, 4, 5, 6, 7, 8, 9, 10, 20, 30, 40, 50, or 100 mammals.

In some embodiments the mammal from where the body fluid is derived is a human.

In some embodiments the mammal is a domestic animal.

In some embodiments the body fluid or element thereof according to the present invention is collected from healthy individual(s).

In some embodiments the body fluid or element thereof according to the present invention is collected from disease individual(s).

In some embodiments the body fluid or element thereof according to the present invention is collected from a combination of healthy and disease individual(s).

In some embodiments the one or more miRNA is upregulated to a concentration level by at least about 50%, such as at least about 100%, such as at least about 200%, such as at least about 300%, such as at least about 400%, such as at least about 500%, such as at least about 600%, such as at least about 700%, such as at least about 800%, as compared to the concentration level of said miRNA in a composition that has not been activated under step b).

In some embodiments the method further comprises a step of incubating the collected body fluid or element thereof in contact with an increased surface area in the presence of synthetic or alternative source of miRNA.

In some embodiments the composition comprising a therapeutically effective amount of one or more miRNA molecule or functional variant thereof, said miRNA being upregulated in a body fluid or element thereof upon activation of said body fluid or element thereof is a composition as defined as defined herein, or prepared by a method according to the present invention.

In some embodiments the administering is by intravenous, intramuscular, intraarticular, transcutaneous, subcutaneous, intranasal, peroral, perineural, intrathecal administration, or by local injection or instillation, for example during a surgical procedure, or a combination of any of these.

In some embodiments the composition according to the present invention is autologous to the subject in need of said treatment.

In some embodiments the composition according to the present invention is homologous to the subject in need of said treatment.

In some embodiments the composition according to the present invention is heterologous to the subject in need of said treatment.

In some embodiments the composition is prepared by a method according to the present invention, wherein said body fluid or element thereof is incubated between 1 and 150, such as 1 and 100 hours prior to the administering of the composition contained therein.

In some embodiments the subject in need of a treatment according to the present invention is a human.

In some embodiments the medical condition that may be treated by the methods of the present invention is selected from the list consisting of cancer, such as leukaemia, paradentosis, abortus habitualis, colitis ulcerosa, polymyalgia rheumatica, whiplash-associated disorders, endometriosis, such as adenomyosis, Parkinson's disease, Alzheimer's disease, dementia, diabetes, such as diabetes I, AIDS/HIV, osteoporosis, psoriasis, and wound healing.

In some embodiments the medical condition that may be treated by the methods of the present invention is Acquired immune deficiency syndrome or acquired immunodeficiency syndrome (AIDS) caused by the human immunodeficiency virus (HIV). In some specific embodiments the methods of the present invention prevents the development of symptoms associated with infections with HIV.

In some embodiments the nucleic acid molecule used according to the present invention is a miRNA.

In some embodiments the nucleic acid molecule used according to the present invention is a pri-miRNA.

In some embodiments the nucleic acid molecule used according to the present invention is a pre-miRNA.

In some embodiments the nucleic acid molecule used according to the present invention is a Small interfering RNA (siRNA).

In some embodiments the methods for the treatment or for alleviating the symptoms of a disease or disorder associated with inflammation, a disease of the immune system, such as undesirable activation of the immune system and/or cancer or other indications associated with abnormal cell growth or cell division further comprises the administration of a chemotherapeutic agent.

In some embodiments the chemotherapeutic agent is selected from a group consisting of: alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxalip latin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-I l); topoisomerase inhibitor RFS 2000; difluoromethylomithine (DMFO); retinoids such as retinoic acid; capecitabine; and pharmaceutically acceptable salts, acids or derivatives of any of the above. In another embodiment, the composition of the invention may comprise other biologically active substances, including therapeutic drugs or pro-drugs, for example, other chemotherapeutic agents, scavenger compounds, antibiotics, anti-virals, anti-fungals, antiinflammatories, vasoconstrictors and anticoagulants, antigens useful for cancer vaccine applications or corresponding pro-drugs.

Numbered Embodiments of the Invention

Embodiment 1. Composition comprising a therapeutically effective amount of one or more nucleic acid molecule encoding a miRNA or functional variant thereof, said miRNA being upregulated in a body fluid or element thereof upon activation of said body fluid or element thereof; for the preparation of a medicament.

Embodiment 2. The composition according to embodiment 1, wherein said miRNA is selected from the group consisting of hsa-miR-320a, hsa-miR-130a, hsa-miR-320c, hsa-miR-628-3p, hsa-miR-637, hsa-miR-320b, hsa-miR-129-5p, hsa-miR-943, hsa-miR-185*, hsa-miR-340*, hsa-miR-744, hsa-miR-638, hsa-miR-585, hsa-miR-26b, hsa-miR-485-3p, hsa-miR-103, hsa-miR-146b-5p, hsa-miR-642, hsa-miR-146a, hsa-let-7a, hsa-let-7f, hsa-miR-200b*, hsa-miR-320d, hsa-let-7d, hsa-miR-1282, hsa-miR-124, hsa-miR-602, hsa-let-7g, hsa-miR-221, hsa-miR-25*, hsa-miR-1184, hsa-miR-663, hsa-miR-93, hsa-miR-30b*, hsa-miR-124*, hsa-miR-22, hsa-miR-1281, hsa-miR-1237, hsa-miR-34b, hsa-miR-1290, hsa-miR-193b*, hsa-miR-526b, hsa-miR-622, hsa-miR-191, hsa-miR-142-3p, hsa-miR-92a, hsa-miR-1280, hsa-miR-1236, hsa-miR-30c, hsa-miR-877*, hsa-miR-548n, hsa-miR-1249, hsa-let-7i, hsa-miR-1224-3p, hsa-miR-17, hsa-miR-300, hsa-miR-193a-5p, hsa-let-7d*, hsa-miR-24, hsa-miR-518c*, hsa-miR-222, hsa-miR-664, hsa-miR-130b, hsa-miR-625*, hsa-miR-593, hsa-miR-885-5p, hsa-miR-505*, hsa-miR-491-3p, hsa-miR-421, hsa-miR-7, hsa-miR-106a, hsa-miR-99b*, hsa-miR-1300, hsa-miR-92b, hsa-miR-30d, hsa-miR-720, hsa-miR-1260, hsa-miR-425, hsa-miR-939, hsa-miR-30a, hsa-miR-30e, hsa-miR-654-5p, hsa-miR-509-5p, hsa-miR-1826 and variants thereof.

Embodiment 3. The composition according to any one of embodiments 1-2, which composition is not derived from a blood product.

Embodiment 4. The composition according to any one of embodiments 1-3, which composition is essentially free of other blood derived components.

Embodiment 5. The composition according to any one of embodiments 1-2, which composition is derived from bone marrow, optionally wherein said bone marrow is purified for blood cells and hematopoietic stem cells.

Embodiment 6. The composition according to any one of embodiments 1-2, which composition is derived from a buffy coat preparation optionally together with plasma.

Embodiment 7. The composition according to any one of embodiments 1-2, which composition is a conditioned cell culture medium, such as an in vitro cell culture medium.

Embodiment 8. The composition according to any one of embodiments 1-7, wherein said miRNA is upregulated in a blood preparation upon activation.

Embodiment 9. The composition according to any of the preceding embodiments, wherein said miRNA is upregulated in a body fluid or element thereof upon activation in a vessel comprising an inductor.

Embodiment 10. The composition according to any of the preceding embodiments, wherein said miRNA is upregulated upon activation on a surface selected from the group consisting of: spheres, gels, glass wool, granulated material and particles or surface structures comprising polystyrene or glass.

Embodiment 11. The composition according to any of embodiments 9-10, wherein the inductor comprises immunoglobulin.

Embodiment 12. The composition according to any one of embodiments 1-11, wherein said nucleic acid molecule is prepared by synthetic means.

Embodiment 13. The composition according to any one of embodiments 1-12, wherein said nucleic acid molecule is present in a measurable amount.

Embodiment 14. The composition according to any one of embodiments 1-13, wherein said nucleic acid molecule comprises affinity-enhancing nucleotide analogous, such as a peptide nucleic acid (PNA), pseudo-complementary PNA (pcPNA), locked nucleic acid (LNA) or analogue thereof.

Embodiment 15. The composition according to any one of embodiment 1-14, which composition comprises at least 1-100, such as at least 2-50, such as at least 10-50 different nucleic acid molecules encoding each different species of a miRNA.

Embodiment 16. The composition according to any one of embodiment 1-15, which composition further comprises a preparation of exosomes, such as an exosome preparation produced by in vitro.

Embodiment 17. The composition according to embodiment 16, wherein said exosomes are enriched with said nucleic acid molecule.

Embodiment 18. Composition comprising a therapeutically effective amount of one or more nucleic acid molecule encoding a miRNA or functional variant thereof, said miRNA being upregulated in a body fluid or element thereof upon activation of said body fluid or element thereof; for the preparation of a medicament for the treatment of an indication selected from the list consisting of a disease or disorder associated with inflammation, a disease of the immune system, such as undesirable activation of the immune system, cancer or other indications associated with abnormal cell growth or cell division, such as leukaemia, chronic inflammation, paradentosis, abortus habitualis, colitis ulcerosa, polymyalgia rheumatica, whiplash-associated disorders, endometriosis, such as adenomyosis, Parkinson's disease, Alzheimer's disease, dementia, diabetes, such as diabetes I, AIDS/HIV, osteoporosis, psoriasis, and wound healing, conditions in the reproduction system, such as low sperm production, development of sertoli cell only syndrome, and abortions of fetus on human and animals.

Embodiment 19. A method for the preparation of a composition comprising a therapeutically effective amount of one or more nucleic acid molecule encoding a miRNA or functional variant thereof, said miRNA being upregulated in a body fluid or element thereof upon activation of said body fluid or element thereof, the method comprising the steps of
a) Collecting said body fluid or element thereof from a mammal;
b) Incubating the collected body fluid or element thereof in contact with an increased surface area.

Embodiment 20. A method for the preparation of a composition comprising a therapeutically effective amount of one or more nucleic acid molecule encoding a miRNA or functional variant thereof, said miRNA being upregulated in a body fluid or element thereof upon activation of said body fluid or element thereof, the method comprising the steps of
a) Collecting said body fluid or element thereof from a mammal;
b) Incubating the collected body fluid or element thereof in contact with an increased surface area;
c) Identifying one or more miRNA upregulated in said body fluid or element thereof;
d) Providing said one or more nucleic acid molecule encoding said miRNA identified in step c) in isolated form and adding them to said composition.

Embodiment 21. The method according to any one of embodiments 19 or 20, wherein said body fluid or element thereof is an in vitro cell culture, such as a monocyte cell culture, a hematopoietic stem culture or cell cultures of placental origin.

Embodiment 22. The method according to any one of embodiments 19 or 20, wherein said body fluid or element thereof is a blood serum preparation.

Embodiment 23. The method according to any one of embodiments 19 or 20, wherein said body fluid or element thereof is a buffy coat preparation.

Embodiment 24. The method according to any one of embodiments 19 or 20, wherein said body fluid or element thereof is whole blood preparation.

Embodiment 25. The method according to any one of embodiments 19 or 20, wherein said body fluid or element thereof is from bone marrow exudates.

26. The method according any one of embodiments 19-25, wherein the activated body fluid or element thereof is further mixed with platelet-rich plasma (PRP), optionally in combination with a preparation of exosomes.

27. The method according to any one of embodiments 19-26, wherein the body fluid or element thereof is activated in a process that further comprises a step of treating said body fluid or element thereof with an anticoagulant.

28. The method according to any one of embodiments 19-27, wherein said body fluid or element thereof is collected from two or more mammals, such as from more than 3, 4, 5, 6, 7, 8, 9, 10, 20, 30, 40, 50, or 100 mammals.

Embodiment 29. The method according to any one of embodiments 19-28, wherein the mammal is a human.

Embodiment 30. The method according to any one of embodiments 19-29, wherein the mammal is a domestic animal.

Embodiment 31. The method according to any one of embodiments 19-30, wherein said body fluid or element thereof is collected from healthy individual(s).

Embodiment 32. The method according to any one of embodiments 19-31, wherein said body fluid or element thereof is collected from disease individual(s).

Embodiment 33. The method according to any one of embodiments 19-31, wherein said body fluid or element thereof is collected from a combination of healthy and disease individual(s).

Embodiment 34. The method according to any one of embodiments 19-33, wherein said one or more miRNA is upregulated to a concentration level by at least about 50%, such as at least about 100%, such as at least about 200%, such as at least about 300%, such as at least about 400%, such as at least about 500%, such as at least about 600%, such as at least about 700%, such as at least about 800%, as compared to the concentration level of said miRNA in a composition that has not been activated under step b).

Embodiment 35. The method according to any one of embodiments 19-34, which method further comprises a step of incubating the collected body fluid or element thereof in contact with an increased surface area in the presence of synthetic or alternative source of miRNA.

Embodiment 36. The method according to any one of embodiments 19-35, which method further comprises incubation of said body fluid or element thereof in a cell growth medium.

Embodiment 37. Kit of parts comprising
a) a device for preparing a composition comprising a therapeutically effective amount of one or more nucleic acid molecule encoding a miRNA or functional variant thereof, said miRNA being upregulated in a body fluid or element thereof upon activation of said body fluid or element thereof, the device comprising a vessel with an inductor; and
b) instructions for use according to the method of any one of embodiments 19-36.

Embodiment 38. A method for the treatment or for alleviating the symptoms of a disease or disorder associated with inflammation, a disease of the immune system, such as undesirable activation of the immune system and/or cancer or other indications associated with abnormal cell growth or cell division, the method comprising administration of a composition comprising a therapeutically effective amount of one or more nucleic acid molecule encoding a miRNA or functional variant thereof, said miRNA being upregulated in a body fluid or element thereof upon activation of said body fluid or element thereof to a subject in need of said treatment.

Embodiment 39. The method according to embodiment 38, wherein said composition comprising a therapeutically effective amount of one or more nucleic acid molecule encoding a miRNA or functional variant thereof, said miRNA being upregulated in a body fluid or element thereof upon activation of said body fluid or element thereof is a composition as defined in any one of embodiments 1-18, or prepared by a method according to any one of embodiments 19-36.

Embodiment 40. The method according to any of embodiments 38 or 39, wherein said administration is by intravenous, intramuscular, intraarticular, transcutaneous, subcutaneous, intranasal, peroral, perineural, intrathecal administration, or by local injection or instillation, for example during a surgical procedure.

Embodiment 41. The methods according to any one of embodiment 38-40, wherein said composition is autologous to the subject in need of said treatment.

Embodiment 42. The methods according to any one of embodiment 38-40, wherein said composition is homologous to the subject in need of said treatment.

Embodiment 43. The methods according to any one of embodiment 38-40, wherein said composition is a heterologous to the subject in need of said treatment.

Embodiment 44. The method according to any of embodiments 38-43, wherein the composition is prepared by a method according to any one of embodiments 19-36, wherein said body fluid or element thereof is incubated between 1 and 100 hours prior to the administering of the composition contained therein.

Embodiment 45. The method according to any one of embodiments 38-44, wherein the subject is a human.

Embodiment 46. The method according to any one of embodiments 38-45, wherein the medical condition is selected from the list consisting of cancer, such as leukaemia, paradentosis, abortus habitualis, colitis ulcerosa, polymyalgia rheumatica, whiplash-associated disorders, endometriosis, such as adenomyosis, Parkinson's disease, Alzheimer's disease, dementia, diabetes, such as diabetes I, AIDS/HIV, osteoporosis, psoriasis, and wound healing.

Embodiment 47. The method according to any one of embodiments 38-46, wherein said method for the treatment further comprises the administration of a chemotherapeutic agent.

EXAMPLES

Example 1

Preparation of Activated Serum

Blood is collected from either an animal or human being or alternatively a population of animals or human beings, preferably without any infection or fewer. The blood is taken by a venous transcutane puncture and collected in a container. Hereafter whole blood or alternatively buffy coat with or without plasma is transferred to a container with a surface, or containing an activating substances such as glass beats etc, preferably a 60 ml container suitable for centrifugation comprising two rubber ports for injection and a small hole for pressure equalization, the container being with or without 2-25 gram of glass beads, 1-8 mm, such as 4 mm.

In some embodiments a buffy coat preparation with or without a plasma fraction is incubated together with a growth medium. This may be either prior to or during the procedure exposing the body fluid to the activating surfaces.

The sample is regurgitating or in any other procedure exposing the blood cells to the activating surfaces for 1, 2, 4, 10, 24, 48, 72, 96, 120, or 150 hours in 37 degrees celcius.

Hereafter the incubation is terminated by lowering the temperature to room temperature and separating the serum from the clotted blood by filtration or centrifugation. In some embodiments of the invention the whole blood is incubated using anticoagulants and after the incubation time the serum is collected by centrifugation or filtration.

The prepared serum, plasma or buffy coat preparation is then stored either at room temperature, frozen at −5-18 degrees celcius or otherwise prepared for freezing storage to optimized the preservation of more complex structures as membrane like vesicles etc.

Example 2

Alternative Procedure for the Preparation of Activated Serum

Blood is incubated in sterile 60 ml containers over a time period of 2-72, 96, 120, or 150 hrs, which container contain glass beads (SiliBeads-Borosilicate, Sigmund Linder, Germany). Glass beads are 2-5 mm, such as 2-4 mm in diameter, and are of medical grade. The container are packed with 5-25, such as 18 grams of beads and may be sterilized either by autoclaving or gamma-irradiation.

Blood culture techniques: In all experiments, containers (e.g. 60 ml container) packed with beads are filled with freshly drawn human whole blood from healthy, male or female donors, between 20 and 70 years old, without anticoagulants unless mentioned otherwise. Whole blood cultures are established under sterile, laminar flow conditions. Incubation is carried out aseptically at 37° C., 5% $CO_2$ for 2-72 hrs intervals. After incubation, serum is retrieved and centrifuged (4200 rpm, 10 min). Alternatively after incubation the serum is separated from the blood cells by centrifugation at 5000 g for 10 min.

Example 3

Treatment of Human Subjects with Activated Blood Serum

Patients are given epidural perineural or intramuscular injections three times once a week. Objective and subjective assessments are made at six times (t1-t6) per patient including visual analog scale (VAS) (Joyce et al., Eur J Clin Pharmacol. 14:415-20 (1975)), Oswestry Pain Questionnaire (Fairbank et al. Spine, 25:2940-2953 (2000)), SF-36 (short form health survey) (Ware et al., Med. Care, 30:473-483 (1992)), and standardized clinical examination. 2 ml of activated serum is injected. One group is given activated serum, another is given 10 mg Triamcinolone, and the last is given 5 mg Triamcinolone. Triamcinolone is a steroid commonly used to treat inflammation, allergies, arthritis, and asthma. It has been shown that Triamcinolone is effective at reducing lumbar radicular pain, (randomized double blind study, Kramer Eur Spine 1997). Similar effects were seen with activated blood preparation as prepared by a method according to any one of examples 1 or 2.

Example 4

5 severe endometriosis patients also having adenomyosis were treated in 6 weeks with conditioned serum prepared as described in example 1 or 2. 5 ml of activated serum were administrated to the patient each intramuscular every week for 5-6 weeks. Their symptoms were significantly relieved.

The background for treating intramuscularly was based on several experimental intramuscular injections in 4 horses during the period of a 2 year. This animal study proved that muscular tenderness was cured by the same intervals of injections.

Example 5

2 abortus habitualis patients were treated during In Vitro Fertilisation (IVF) with the same regime as described under example 4, and one conceived during this study.

Example 6

3 colitis ulcerosa and 1 Crohn patients has been through the same timed preparation and injection of activated serum with significant improvement of their conditions/disease, thus in the acute initial treatment a shorter interval for administration is beneficial and after a plateau phase in the symptoms has been reached, a longer interval between administration of the serum seems to stabilize all symptoms. The benefit of this method of sequential strategy for administration of the substances is to enable the invention to cope with the high activity of the disease in the acute phase and changing the activity of the substances when the disease is in a stable phase.

Further to this, the administration of the activated serum has an impact of the course of the disease by administration of a larger volume of conditioned serum in the start of the treatment regimens, such as 5 ml, 10 ml or 20 ml.

One patient diagnosed with severe colitis ulcerose having defecation 20 times daily, strictures in the bowel, visualized by coloscopy prior to the treatment with activated serum. The patient was completely cured within 7 weeks (certified by an external doctor performing the coloscopy).

Example 7

In vitro culture of stem cell producing mirRNA including cell cultures of placental origin:

Hematopoietic stem cells or cell cultures of placental origin are cultured under in vitro conditions for a period of time optionally in a container containing the activating substances such as glass beats etc Alternatively the cell and cell culture medium may in a subsequent step be transferred to a container containing the activating substance such as glass beats etc.

After regurgitating or in any other procedure exposing the cells to the activating surfaces for 1, 2, 4, 10, 24, or 48 hours in 37 degrees Celsius the sample may be left untouched for a total of 5 hour, to 24 hours depending on the volume, the surface area of the vessel and number of cells in a given sample.

Hereafter the incubation is terminated by lowering the temperature to room temperature.

The prepared cell preparation may then stored either at room temperature, frozen at −5-18 degrees Celsius or otherwise prepared for freezing storage to optimized the preservation of more complex structures as membrane like vesicles etc.

Example 8

Activated serum as prepared by examples 1 or 2 was tested in an assay to determine the specific miRNAs upregulated in response to the activation. A miRCURY™ LNA Array microRNA Profiling Service was performed by Exiqon (Denmark). Results are summarized in table 1.

Table 1 contains normalised Hy3 signals (log 2 transformed) from all hybridizations. Shown is the median of replicated measurements of the same miRNA from each slide.

TABLE 1

| | Log2-transformed values | | Normalized signal medianvalues | | | |
|---|---|---|---|---|---|---|
| | Call rate | | | | Delta Log2- | |
| Annotation | 7% Serum Slide 1 | 7% Activated serum (1/5) Slide 2 | Serum Slide 1 | Activated serum (1/5) Slide 2 | transformed values Activated serum (1/5) versus vs Serum | Fold change Activated serum (1/5) versus vs Serum |
| hsa-miR-320a | 6.93 | 8.20 | 122 | 293 | 1.26 | 2.40 |
| hsa-miR-130a | 5.83 | 7.08 | 57 | 135 | 1.24 | 2.37 |
| hsa-miR-320c | 6.98 | 8.20 | 126 | 295 | 1.23 | 2.34 |
| hsa-miR-628-3p | 7.07 | 8.15 | 134 | 284 | 1.08 | 2.11 |
| hsa-miR-637 | 7.81 | 8.88 | 224 | 473 | 1.08 | 2.11 |
| hsa-miR-320b | 7.27 | 8.31 | 154 | 318 | 1.04 | 2.06 |
| hsa-miR-129-5p | 9.86 | 10.90 | 929 | 1912 | 1.04 | 2.06 |
| hsa-miR-943 | 8.20 | 9.20 | 295 | 586 | 0.99 | 1.99 |
| hsa-miR-185* | 7.88 | 8.87 | 236 | 467 | 0.99 | 1.98 |
| hsa-miR-340* | 6.11 | 7.06 | 69 | 133 | 0.95 | 1.93 |
| hsa-miR-744 | 7.05 | 7.98 | 132 | 252 | 0.93 | 1.90 |
| hsa-miR-638 | 9.89 | 10.81 | 946 | 1796 | 0.93 | 1.90 |
| hsa-miR-585 | 8.03 | 8.95 | 261 | 494 | 0.92 | 1.89 |
| hsa-miR-26b | 6.69 | 7.54 | 103 | 186 | 0.85 | 1.81 |
| hsa-miR-485-3p | 8.20 | 9.01 | 294 | 516 | 0.81 | 1.75 |
| hsa-miR-103 | 5.49 | 6.28 | 45 | 78 | 0.78 | 1.72 |
| hsa-miR-146b-5p | 5.70 | 6.44 | 52 | 87 | 0.74 | 1.67 |
| hsa-miR-642 | 6.28 | 7.02 | 78 | 130 | 0.74 | 1.66 |
| hsa-miR-146a | 5.50 | 6.23 | 45 | 75 | 0.73 | 1.66 |
| hsa-let-7a | 5.87 | 6.60 | 58 | 97 | 0.73 | 1.66 |
| hsa-let-7f | 6.69 | 7.42 | 103 | 171 | 0.73 | 1.66 |
| hsa-miR-200b* | 7.54 | 8.27 | 186 | 308 | 0.73 | 1.65 |
| hsa-miR-320d | 7.22 | 7.93 | 149 | 243 | 0.70 | 1.63 |
| hsa-let-7d | 5.64 | 6.23 | 50 | 75 | 0.59 | 1.50 |
| hsa-miR-1282 | 5.53 | 6.12 | 46 | 69 | 0.58 | 1.50 |
| hsa-miR-124 | 6.54 | 7.11 | 93 | 138 | 0.57 | 1.49 |
| hsa-miR-602 | 10.00 | 10.54 | 1023 | 1489 | 0.54 | 1.46 |
| hsa-let-7g | 5.70 | 6.23 | 52 | 75 | 0.53 | 1.44 |
| hsa-miR-221 | 6.01 | 6.54 | 64 | 93 | 0.53 | 1.44 |
| hsa-miR-25* | 9.02 | 9.54 | 521 | 744 | 0.52 | 1.43 |
| hsa-miR-1184 | 6.65 | 7.16 | 100 | 143 | 0.51 | 1.43 |
| hsa-miR-663 | 6.00 | 6.48 | 64 | 89 | 0.48 | 1.39 |
| hsa-miR-93 | 6.30 | 6.78 | 79 | 110 | 0.47 | 1.39 |
| hsa-miR-30b* | 5.95 | 6.39 | 62 | 84 | 0.44 | 1.36 |
| hsa-miR-124* | 6.66 | 7.10 | 101 | 138 | 0.44 | 1.36 |
| hsa-miR-22 | 8.80 | 9.23 | 445 | 601 | 0.43 | 1.35 |

TABLE 1-continued

| | Log2-transformed values | | Normalized signal medianvalues | | | |
| | Call rate | | | | Delta Log2- | |
| Annotation | 7% Serum Slide 1 | 7% Activated serum (1/5) Slide 2 | Serum Slide 1 | Activated serum (1/5) Slide 2 | transformed values Activated serum (1/5) versus vs Serum | Fold change Activated serum (1/5) versus vs Serum |
|---|---|---|---|---|---|---|
| hsa-miR-1281 | 5.63 | 6.06 | 50 | 67 | 0.42 | 1.34 |
| hsa-miR-1237 | 5.66 | 6.08 | 51 | 68 | 0.42 | 1.34 |
| hsa-miR-34b | 6.40 | 6.82 | 84 | 113 | 0.42 | 1.34 |
| hsa-miR-1290 | 12.98 | 13.39 | 8064 | 10719 | 0.41 | 1.33 |
| hsa-miR-193b* | 8.04 | 8.43 | 264 | 344 | 0.38 | 1.30 |
| hsa-miR-526b | 5.53 | 5.91 | 46 | 60 | 0.38 | 1.30 |
| hsa-miR-622 | 5.79 | 6.17 | 55 | 72 | 0.37 | 1.30 |
| hsa-miR-191 | 7.74 | 8.11 | 214 | 276 | 0.36 | 1.29 |
| hsa-miR-142-3p | 5.63 | 5.98 | 49 | 63 | 0.35 | 1.27 |
| hsa-miR-92a | 5.89 | 6.23 | 59 | 75 | 0.34 | 1.26 |
| hsa-miR-1280 | 7.68 | 8.02 | 206 | 260 | 0.34 | 1.26 |
| hsa-miR-1236 | 5.85 | 6.18 | 58 | 72 | 0.33 | 1.26 |
| hsa-miR-30c | 5.85 | 6.17 | 58 | 72 | 0.32 | 1.24 |
| hsa-miR-877* | 5.71 | 6.02 | 52 | 65 | 0.31 | 1.24 |
| hsa-miR-548n | 5.54 | 5.85 | 47 | 58 | 0.31 | 1.24 |
| hsa-miR-1249 | 6.24 | 6.54 | 75 | 93 | 0.30 | 1.23 |
| hsa-let-7i | 5.90 | 6.19 | 60 | 73 | 0.30 | 1.23 |
| hsa-miR-1224-3p | 5.72 | 6.01 | 53 | 64 | 0.28 | 1.22 |
| hsa-miR-17 | 5.83 | 6.11 | 57 | 69 | 0.28 | 1.21 |
| hsa-miR-300 | 6.14 | 6.42 | 70 | 85 | 0.28 | 1.21 |
| hsa-miR-193a-5p | 5.54 | 5.81 | 47 | 56 | 0.27 | 1.21 |
| hsa-let-7d* | 5.52 | 5.78 | 46 | 55 | 0.27 | 1.20 |
| hsa-miR-24 | 7.43 | 7.69 | 172 | 207 | 0.26 | 1.20 |
| hsa-miR-518c* | 5.62 | 5.88 | 49 | 59 | 0.26 | 1.20 |
| hsa-miR-222 | 5.52 | 5.76 | 46 | 54 | 0.24 | 1.18 |
| hsa-miR-664 | 5.94 | 6.18 | 62 | 73 | 0.24 | 1.18 |
| hsa-miR-130b | 6.26 | 6.48 | 76 | 89 | 0.22 | 1.17 |
| hsa-miR-625* | 5.97 | 6.19 | 63 | 73 | 0.22 | 1.16 |
| hsa-miR-593 | 5.46 | 5.68 | 44 | 51 | 0.22 | 1.16 |
| hsa-miR-885-5p | 5.55 | 5.74 | 47 | 53 | 0.18 | 1.14 |
| hsa-miR-505* | 5.73 | 5.90 | 53 | 60 | 0.17 | 1.13 |
| hsa-miR-491-3p | 5.67 | 5.84 | 51 | 57 | 0.17 | 1.12 |
| hsa-miR-421 | 5.70 | 5.87 | 52 | 58 | 0.16 | 1.12 |
| hsa-miR-7 | 6.33 | 6.49 | 81 | 90 | 0.16 | 1.12 |
| hsa-miR-106a | 5.59 | 5.75 | 48 | 54 | 0.16 | 1.12 |
| hsa-miR-99b* | 6.57 | 6.73 | 95 | 106 | 0.16 | 1.11 |
| hsa-miR-1300 | 6.01 | 6.15 | 65 | 71 | 0.13 | 1.10 |
| hsa-miR-92b | 5.88 | 6.01 | 59 | 65 | 0.13 | 1.09 |
| hsa-miR-30d | 5.89 | 6.02 | 59 | 65 | 0.13 | 1.09 |
| hsa-miR-720 | 10.99 | 11.11 | 2037 | 2212 | 0.12 | 1.09 |
| hsa-miR-1260 | 5.50 | 5.61 | 45 | 49 | 0.11 | 1.08 |
| hsa-miR-425 | 5.63 | 5.69 | 50 | 52 | 0.06 | 1.04 |
| hsa-miR-939 | 8.51 | 8.55 | 363 | 374 | 0.04 | 1.03 |
| hsa-miR-30a | 6.78 | 6.82 | 110 | 113 | 0.03 | 1.02 |
| hsa-miR-30e | 5.96 | 5.99 | 62 | 64 | 0.03 | 1.02 |
| hsa-miR-654-5p | 5.76 | 5.78 | 54 | 55 | 0.02 | 1.01 |
| hsa-miR-509-5p | 6.49 | 6.51 | 90 | 91 | 0.02 | 1.01 |
| hsa-miR-1826 | 10.16 | 10.18 | 1148 | 1157 | 0.01 | 1.01 |

Example 9

Reduction of Tumour Cell Proliferation In Vitro

Study of impact on growth of human and equine malignant melanoma cells after exposure to activated serum.

Cells of a primary tumour from human and equine malignant melanoma tissue was grafted and put in to passage by in vitro growth.

Serum from human and horse was activated for 24 hours or 48 hours as described in example 1 or 2.2%, 5%, or 10% of the activated serum was applied to the growth medium of the primary tumour cells Cell proliferation of the primary tumour cells as measured by cell counts was significantly reduced in vitro after exposure to the activated serum.

Example 10

In Vivo Tumour Mass Reduction

Serum was prepared as described in example 1 or 2 with 48 hours of activation.

In an equine study on 4 malignant melanoma tumors of less than 1 cm in diameter in the skin, the horse was injected in the melanoma with 2 or 5 ml of activated serum (48 h) prepared from another horse, 3 times with an interval of 3 days. All melanomas disappeared completely.

In the same horse one large melanoma (hwd: 5 cm×1 cm×1 cm) was injected into the melanoma with 2 ml of serum prepared from another horse. Injections were repeated 4 times. The melanoma decreased significantly in size to hwd: 2 cm×0.4 cm×1 cm.

In a further study a gray gelding age 10 yrs was intramuscularly injected with serum preparation (incubation 48 h) a total of 5 ml every week for 6 weeks. During this period malignant melanoma plaque around anus was totally abolished and not longer seen. A period of 2 month observation time was followed without relapse.

Example 11

4 horses with cutaneous affection of sarcoid tumors are injected with 5 ml of serum (48 h incubation) ever 5th day for a periode of 10 weeks. The tumor will disappear.

Example 12

Primary tumour cells prepared as described in example 9 was added in a concentration of 10.000 to 100.000 cells per ml to serum in conjunction with the activation of the serum. A significant enrichment (up to 50% higher) in miRNA of the prepared serum was seen as compared to a serum control without tumour cells.

Example 13

An increased content of miRNA in human serum preparation was seen, when the time period of incubation was up to 150 h of incubation.

Human serum was activated as described in example 1 or 2 however with a period of 150 hours of incubation of the human serum. The samples were analysed for amounts compared to a control sample by quantitative PCR. The following miRNAs were seen to be upregulated 1.5 to 680 times: hsa-Let-7a, hsa-Let-7b, hsa-Let-7b*, hsa-Let-7c, hsa-Let-7d, hsa-Let-7d*, hsa-Let-7e, hsa-Let-7f, hsa-Let-7f*, hsa-Let-7g, hsa-Let-7g*, hsa-Let-7i, hsa-miR-103, hsa-miR-106A, hsa-miR-106B, hsa-miR-107, hsa-miR-125A, hsa-miR-125B, hsa-miR-126, hsa-miR-128, hsa-miR-130A, hsa-miR-130B, hsa-miR-140-3P, hsa-miR-140-5P, hsa-miR-142-3P, hsa-miR-142-5P, hsa-miR-143, hsa-miR-144, hsa-miR-146A, hsa-miR-148A, hsa-miR-148B, hsa-miR-150, hsa-miR-151-3P, hsa-miR-151-5P, hsa-miR-152, hsa-miR-15A, hsa-miR-15B, hsa-miR-16, hsa-miR-15B*, hsa-miR-17, hsa-miR-181A, hsa-miR-185, hsa-miR-186, hsa-miR-18A, hsa-miR-18A*, hsa-miR-18B, hsa-miR-192, hsa-miR-191, hsa-miR-194, hsa-miR-197, hsa-miR-1979, hsa-miR-19A, hsa-miR-19B, hsa-miR-20A, hsa-miR-20B, hsa-miR-21, hsa-miR-205, hsa-miR-210, hsa-miR-215, hsa-miR-22, hsa-miR-22*, hsa-miR-221, hsa-miR-222, hsa-miR-223, hsa-miR-223*, hsa-miR-23A, hsa-miR-23B, hsa-miR-24, hsa-miR-25, hsa-miR-26A, hsa-miR-26B, hsa-miR-27A, hsa-miR-27B, hsa-miR-28-5P, hsa-miR-29A, hsa-miR-29B, hsa-miR-29C, hsa-miR-30A, hsa-miR-301A, hsa-miR-30B, hsa-miR-30C, hsa-miR-30D, hsa-miR-30E, hsa-miR-320A, hsa-miR-320B, hsa-miR-324-3P, hsa-miR-326, hsa-miR-328, hsa-miR-338-3P, hsa-miR-342-3P, hsa-miR-339-5P, hsa-miR-33A, hsa-miR-342-3P, hsa-miR-365, hsa-miR-378, hsa-miR-423-3P, hsa-miR-423-5P, hsa-miR-424, hsa-miR-425, hsa-miR-451, hsa-miR-484, hsa-miR-486-5P, hsa-miR-505, hsa-miR-502-3P, hsa-miR-590-5P, hsa-miR-628-3P, hsa-miR-652, hsa-miR-660, hsa-miR-720, hsa-miR-92A, hsa-miR-92B, hsa-miR-93, hsa-miR-93*, hsa-miR-99A, hsa-miR-99B, hsa-miR-103-2*, hsa-miR-106B*, hsa-miR-133A, hsa-miR-133B, hsa-miR-338-3P, hsa-miR-340, hsa-miR-34A, hsa-miR-34B, hsa-miR-376A, hsa-miR-532-3P, hsa-miR-125A-5P, hsa-miR-154, hsa-miR-196B, hsa-miR-1979, hsa-miR-326, hsa-miR-425*, hsa-miR-127-3P, hsa-miR-1537, hsa-miR-183, hsa-miR-29B-2*, hsa-miR-339-3P, hsa-miR-551A, hsa-miR-629, hsa-miR-766, hsa-miR-2110, hsa-miR-361-3P, hsa-miR-501-5P, hsa-miR-940, hsa-miR-1249, hsa-miR-132, hsa-miR-1538, and hsa-miR-149.

Example 14

Capture of miRNA by Magnetic Beads

Serum prepared according to example 1 or 2 with 96 hours of activation period and with a pre-known enriched amount of miRNA was mixed at ratio 1:1 with polyethyleneimine (PEI) coated iron magnetic nanoparticles (Chemicell Gmbh, Berlin, Germany) essentially as described in Huttinger et al 3. Gene Med 2008; 10:655-667. The preparation was gently mixed for 20 minutes. The magnetic nanoparticles were drawn to the side of the container using a neodymium-iron-boron magnet (Neo Delta magnet NE2010; IBS magnet, Berlin, Germany). The liquid supernatant free of nanoparticles was recovered and analysed for miRNA be quantitative PCT. The amounts of miRNA in the supernatant were reduced between 50-80% compared to pre-mixing levels. The positively charged magnetic nanoparticles mediated binding of miRNA via electrostatic interactions. Serum with enriched amounts of miRNA mixed with magnetic nanoparticles or magnetic nanoparticles following mixing with miRNA enriched serum after removal of the supernatant, may be used to position in or close to the tumor in vivo after injection in the peripheral place using magnets over the tumour.

The invention claimed is:

1. A method for the preparation of a composition comprising a therapeutically effective amount of one or more miRNA molecule, the method comprising the steps of:
    a) collecting blood or blood serum from a mammal;
    b) activating said blood or blood serum wherein said activating step comprises incubating the collected blood or blood serum in contact with an increased surface area for more than 24 hours, wherein said one or more miRNA molecule is present in the blood or blood serum in a higher measurable concentration after the activation compared to the measurable concentration of the one or more miRNA molecule present in blood or blood serum not having been activated;
    c) collecting said body fluid produced after step b) comprising a higher measureable concentration of said miRNA molecule; and
    d) preparing a composition comprising a therapeutically effective amount of said upregulated miRNA molecule.

2. A method for the preparation of a composition comprising a therapeutically effective amount of one or more miRNA molecule, the method comprising the steps of:
    a) collecting body fluid or element thereof from a mammal;
    b) activating said body fluid or element thereof wherein said activating step comprises incubating the collected body fluid or element thereof in contact with an increased surface area for more than 24 hours, wherein said one or more miRNA molecule is upregulated compared to miRNA produced from body fluid or an element thereof not having been activated;
    c) identifying one or more miRNA molecule upregulated in said body fluid or element thereof compared to miRNA produced from body fluid or an element thereof not having been activated; and
    d) preparing a composition comprising a therapeutically effective amount of said upregulated miRNA molecule identified in step c) in isolated form.

3. The method according to claim 1, wherein said blood or blood serum is selected from a blood serum preparation or a whole blood preparation.

4. The method according to claim 1, wherein the mammal is a human.

5. The method according to claim 1, wherein the mammal is a domestic animal.

6. The method according to claim 1, wherein said blood or blood serum is collected from a combination of healthy and diseased individual(s).

7. The method according claim 1, wherein the measureable concentration of said one or more miRNA is increased by at least about 50%, as compared to the measurable concentration level of said miRNA in a composition that has not been activated under step b).

8. The method according claim 1, which method further comprises a step of incubating the collected blood or blood serum in contact with an increased surface area in the presence of synthetic or alternative source of miRNA.

9. The method according to claim 1, which method further comprises incubation of said blood or blood serum in a cell growth medium.

10. The method according to claim 1, wherein said composition further comprises a preparation of magnetic nanoparticles, such as polyethyleneimine (PEI) coated iron magnetic nanoparticles.

11. The method according to claim 1, wherein miRNA in said higher measurable concentration is purified from said blood or blood serum in step b), and wherein a therapeutically effective amount of said purified miRNA is used in the preparation of said composition in step d).

* * * * *